United States Patent
Monbouquette

(10) Patent No.: US 6,241,863 B1
(45) Date of Patent: Jun. 5, 2001

(54) AMPEROMETRIC BIOSENSORS BASED ON REDOX ENZYMES

(76) Inventor: Harold G. Monbouquette, UCLA Dept. of Chemical Engineering, 5531 Boelter Hall, Los Angeles, CA (US) 90095-1406

(*) Notice: Subject to any disclaimer, the term of this patent is extended or adjusted under 35 U.S.C. 154(b) by 0 days.

(21) Appl. No.: 09/300,284

(22) Filed: Apr. 27, 1999

Related U.S. Application Data

(60) Provisional application No. 60/083,231, filed on Apr. 27, 1998.

(51) Int. Cl.[7] .................................................. G01N 27/26
(52) U.S. Cl. ........................................ 204/403; 427/2.11
(58) Field of Search ........................ 204/403; 427/2.11; 435/817

(56) References Cited

U.S. PATENT DOCUMENTS 5,611,900 * 3/1997 Worden et al. ...................... 204/403

OTHER PUBLICATIONS

Electrochemistry for Chemists, 2nd. ed., Sawyer et al., John Wiley & Sons, month unknown 1995, pp. 188–189.*

Kinnear, K.T.; Monbouquette, H.G. Direct electron transfer to *Escherichia coli* fumarate reductase in self–assembled alkanethiol monolayers on gold electrodes. Langmuir month unknown 1993, 9, 2255–2257.

Kinnear, K.T.; Monbouquette, H.G. Electroenzymatic sensing of fructose using fructose dehydrogenase immobilized in a self–assembled monolayer on gold. In Biosensor and Chemical Sensor Technology: Process Monitoring and Control, Rogers, K.R.; Mulchandani, A.; Zhou, W.; Editors. ACS: Washington DC, month unknown 1995, 82–86.

Nakashima, K.; Takei, H.; Adachi, O.; Shinagawa, E.; Ameyama, M. Determination of seminal–fructose using D–fructose dehydrogenase. Clin. Chim. Acta month unknown 1985, 151, 307–310.

Ameyama, M., Shinagawa, E.; Matsushita, K.; Adachi, O. D–Fructose dehydrogenase of *Gluconobacter industrius*: Purification, characterization, and application to enzymatic microdetermination of D–fructose. J. Bacteriol. month unknown 1981, 145, 814–823.

Prado, F.E.; Sampietro, A.R. A method for the determination of fructose using a single enzyme: production and properties of fructose dehydrogenase from *Gluconobacter industrius*. Biotechnol. Appl. Biochem. month unknown 1994, 19, 361–368.

(List continued on next page.)

*Primary Examiner*—T. Tung
*Assistant Examiner*—Alex Noguerola
(74) *Attorney, Agent, or Firm*—Sheldon & Mak

(57) ABSTRACT

The invention includes various prototypical amperometric biosensors for the quantification of biological substrates such as fructose, creatinine, creatine, and sarcosine, and the methods for producing these biosensors. Also included in the invention is a minaturized version of the biosensing devices. The components of these prototypical biosensors are immobilized on a self-assembled monolayer (SAM) comprising chemisorbed alkanethiols. The deposition of an amphiphilic lipid layer to these systems increases the stability and activity of the resultant biosensor and enhances the rejection of many interferents. An additional feature of the invention is the co-deposition of the components of the sensor via a novel detergent dialysis protocol. The invention features two particular biosensor systems. One embodiment involves fructose dehydrogenase as the redox/sensor enzyme and fructose as the substrate/analyte. Another embodiment involves the measurement of the substrates/analytes, creatinine, creatine and sarcosine, using sacrosine dehydrogenase as the redox/sensor enzyme, with the involvement of creatinine amidohydrolase and/or creatine amidinohydrolase in the reaction pathway.

27 Claims, 18 Drawing Sheets

OTHER PUBLICATIONS

Stelzle, M.; WeissmYller, G.; Sackmann, E. On the Application of Supported Bilayers as Receptive Layers for Biosensors with Electrical Detection. J. Phys. Chem. month unknown 1993, 97, 2974–2981.

Cullison, J.K.; Hawkridge, F.M.; Nakashima, N.; Hartzell, C.R. The direct electron transfer reactions of cytochrome oxidase immobilized into a membrane modified electrode. In Charge and Field Effects in Biosystems—3, Allen, M.J.; Cleary, S.F.; Sowers, A.E.; Shillady, D.D.; Edditors. Birkh-Suser: Boston, month unknown 1992; 29–40.

Cullison, J.K. Hawkridge, F.M.; Nakashima, N.; Yoshikawa, S. A Study of cytochrome c oxidase in lipid bilayer membranes on electrode surfaces. Langmuir month unknown 1994, 10, 877–882.

Plant, A.L. Self–assembled phospholipid/alkanethiol biomimetic bilayers on gold. Langmuir month unknown 1993, 9, 2764–2767.

Song, S.; Clark, R.A.; Bowden, E.F.; Tarlov, M.J. Characterization of *Cytochrome c*/Alkanethiolate Structures Prepared by Self–Assembly on Gold. J. Phys. Chem. month unknown 1993, 97, 6564–6572.

Tien, H.T. Self–Assembled Lipid Bilayers for Biosensors and Molecular Electronic Devices. Adv. Mat. month unknown 1990, 2, 316–318.

Tien, H.T.; Salamon, Z. Formation of Self–Assembled Lipid Bilayers on Solid Substrates. Bioelectrochem. Bioenerg. month unknown 1989, 22, 211–218.

Ikeda, T., Matsushita, F., Senda, M. d–Fructose Dehydrogenase–Modified Carbon Paste Electrode Containing p–Benzoquinone as a Mediated Amperometric Fructose Sensor. Agric. Biol. Chem. month unknown 1990, 54, 2919–2924.

Ikeda, T.; Matsushita, F.; Senda, M. Amperometric fructose sensor based on direct bioelectrocatalysis. Biosensors Bioelectron. 1991, 6, 299–304.

Matsumoto, K.; Baeza Baeza, J.J.; Mottola, H.A. Simultaneous kinetic–based determination of fructose and ascorbate with a rotating bioreactor and amperometric detection: Application to the analysis of food samples. Anal. Chem. Jul. 1993, 65, 1658–1661.

Parellada, J.; Dom'nguez, E.; Fern≠ndez, V.M. Amperometric flow injection determination of fructose in honey with a carbon paste sensor based on fructose dehydrogenase. Anal. Chim. Acta. month unknown 1996, 330, 71–77.

Khan, G.F.; Shinohara, H.; Ikariyama, Y.; Aizawa, M. Electrochemical behaviour of monolayer quinoprotein absorbed on the electrode surface. J. Electroanal. Chem. month unknown 1991, 315, 263–273.

Khan, G.F.; Kobatake, E.; Shinohara, H.; Ikariyama, Y.; Aizawa, M. Molecular interface for an activity controlled enzyme electrode and its application for the determination of fructose. Anal. Chem. 1992, 64, 1254–1258, June.

Begum, A,; Kobatake, E.; Suzawa, T.; Ikariyama, Y.; Aizawa, M. New electrocatalytic biomolecular interface for fabricating a fructose dehydrogenase–based sensing system. Anal. Chim. Acta month unknown 1993, 280, 31–36.

Ikeda, T.; Matsushita, F.; Senda, M. D–Fructose dehydrogenase–modified carbon paste electrode containing p–benzoquinone as a mediated amperometric fructose sensor. Agric. Biol. Chem. month unknown 1990, 54, 2919–2924.

Garcia, C.A.B.; de Oliveira Neto, G.; Kubota, L.T.; Grandin, L.A. A new amperometric biosensor for fructose using a carbon paste electrode modified with silica gel coated with Meldola's Blue and fructose 5–dehydrogenase. J. Electroanal. Chem. month unknown 1996, 418, 147–151.

Yabuki, S., Mizutani, F. D–Fructose Sensing Electrode Based on Electron Transfer of D–Fructose Dehydrogenase at Colloidal Gold–Enzyme Modified Electrode. Electroanal. month unknown 1997, 9, 23–25.

Paredes, P.A., Parellada, J., Fern≠ndez, V.M., Katakis, I., Dominguez, E. Amperometric mediated carbon paste biosensor based on D–fructose dehydrogenase for the determination of fructose in food analysis. Biosens. Bioelectron. month unknown 1997, 12, 1233–1243.

Swann, M.J., Bloor, D., Haruyama, T., Aizawa, M. The role of ploypyrrole as charge transfer mediator and immobilization matrix for D–fructose dehydrogenase in a fructose sensor. Biosens. Bioelectron. month unknown 1997, 12, 1169–1182.

Antiochia, R., Palleschi, G. A Tri–Enzyme Electrode Probe for the Sequential Determination of Fructose and Glucose in the Same Sample. Anal. Lett. month unknown 1997, 30, 683–697.

Guilbault, G.G.; Coulet, P.R. Creatinine–selective enzyme electrodes. Anal. Chim. Acta. month unknown 1983, 152, 223–228.

Khan, G.F.; Wernet, W. A highly sensitive amperometric creatinine sensor. Anal. Chim. Acta. month unknown 1997, 351, 151–158.

Koncki, R.; Walcerz, I.; Ruckruh, F.; Glab, S. Bienzymatic potentiometric electrodes for creatine and L–arginine determination. Anal. Chim. Acta. month unknown 1996, 333, 215–222.

Kubo, I.; Karube, I.; Suzuki, S. Amperometric determination of creatinine with a biosensor based on immobilized creatininase and nitrifying bacteria. Anal. Chim. Acta. month unknown 1983, 151, 371–376.

Madaras, M.B.; Buck, R.P. Miniaturized biosensors employing electropolymerized permselective films and their use for creatinine assays in human serum. Anal. Chem. Nov. 1996, 68, 3832–3839.

Mascini, M.; Fortunati, S.; Moscone, D.; Palleschi, G. Ammonia Abatement in an enzymatic flow system for the determination of creatinine in blood sera and urine. Anal. Chim. Acta. month unknown 1985, 171, 175–184.

Meyerhoff, M.; Rechnitz, G.A. An activated enzyme electrode for creatinine. Anal. Chim. Acta. month unknown 1976, 85, 277–285.

Montonaka, J.; Takabayashi, H.; Ikeda, S.; Tanaka, N. Preparation and properties of a micro enzyme sensor for creatine. Anal. Lett. month unknown 1991, 23, 1981–1991.

Nguyen, V.K.; Wolff, C.–M.; Seris, J.L.; Schwing, J.–P. Immobilized enzyme electrode for creatinine determination in serum. Anal. Chem., Mar. 1991, 63, 611–614.

Sakslund, H.; Hammerich, O. Effects of pH, temperature, and reaction products on the performance of an immobilized creatininase–creatinase–sarcosine oxidase enzyme system for creatinine determination. Anal. Chim. Acta. month unknown 1992, 268, 331–345.

Schneider, J.; Grundig, B.; Renneberg, R.; Cammann, K.; Madaras, M.B.; Buck, R.P.; Vorlop, K.–D. Hydrogel matrix for three enzyme entrapment in creatine/creatinine amperometric biosensing. Anal. Chim. Acta. month unknown 1996, 325, 161–167.

Tsuchida, T.; Yoda, K. Multi–enzyme membrane electrodes for determination of creatinine and creatine in serum. Clin. Chem. month unknown 1983. 29, 51–55.

Winquist, F.; Lundstrom, I. Determination of creatinine by an ammonia–sensitive semiconductor structure and immobilized enzymes. Anal. Chem. month unknown 1986, 58, 145–148.

Yamato, H.; Ohwa, M.; Wernet, W. A polypyrrole/three–enzyme electrode for creatinine determination. Anal. Chem. 1995, 67, 2776–2780, Sep.

Oka, I.; Yoshimoto, T.; Rikitake, K.; Ogushi, S.; Tsuru, D. Sarcosine dehydrogenase form *Pseudomonas putida*: purification and some properties. Agric. Biol. Chem., month unknown 1979, 43, 1197–1203.

Tsuru, D.; Oka, I.; Yoshimoto, T. Creatinine decomposing enzymes in *Pseudomonas putida*. Agric. Biol. Chem. month unknown 1976, 40, 1011–1018.

Broun, G.B. Chemically Aggregated Enzymes. Meth. Enzymol. month unknown 1976, 44,263–280. and refs 31, 32, 34–36, 38 under creatine/creatinine biosensors.

Riklin, A.; Willner, I. Glucose and acetycholine sensing multilayer enzyme electrodes of controlled enzyme layer thickness. Anal. Chem. Nov. 1995, 67, 4118–4126.

Katz, E.; Riklin, A.; Willner, I. Application of stilbene–(4, 4'–diisothiocyanate–2,2'–disulfonic acid as a bifunctional reagent for the organization of organic materials and proteins onto electrode surfaces. J. Electroanal. Chem. 1993, 354, 129–144.

Kinnear, K.T.; Monbouquette, H.G. An amperometric fructose biosensor based on fructose dehydrogenase immobilized in a membrane mimetic layer on gold. Abstract published in *Advance ACS Abstracts*, Apr. 1, 1997.

\* cited by examiner

AMPEROMETRIC BIOSENSORS BASED ON REDOX ENZYMES

CROSS REFERENCE TO RELATED APPLICATION

This present application is a Continued-In-Part of United States Provisional Application filed Apr. 27, 1998, application No. 60/083,231, the contents of which are incorporated herein by reference in its entirety.

This invention with at least partial Government funding under Grant No. BES-9400523 from the National Science Foundation. The United States Government may have rights in the invention.

BACKGROUND OF THE INVENTION

The present relates to amperometric biosensors capable of rapidly quantifying the concentration of an analyte in a sample solution with high accuracy in a simplified manner, and to methods of producing same. In particular, the invention relates to amperometric biosensors having an immobilized, redox enzyme as a enzymatic sensing element coupled to a metal electrode.

A biosensor is an analytical device incorporating biological and chemical sensing elements, either intimately connected to or integrated with a suitable transducer, which enables the conversion of concentrations of specific chemicals into electronic signals. A majority of biosensors produced thus far have incorporated an enzyme as a biological recognition component.

A critical element in the design of a successful biosensor is the immobilization procedure for biological components. Generally, four main approaches to enzyme immobilization have been utilized. These include: (1) physical adsorption at a solid surface, (2) entrapment in polymeric gels or microcapsules, (3) cross-linking by means of bifunctional reagents, and (4) covalent binding to a reactive insoluble support. Although these methods are generally used in the construction of biosensing devices, specific details in the immobilization and assembly protocols also may be crucial to the development of reliable, as well as sensitive biosensors.

This main challenge in biosensor technology is to find an effective means to couple the biological component to the transducer. This coupling is particularly important to the development of amperometric biosensors, since conventional metal electrodes are generally very poor voltammetric electrodes for the direct oxidation or reduction of biological components. The approaches used to modify these electrodes for use as biosensors can be divided into two groups: (1) modification of the electrode surface by deposition of a monolayer, which is based upon either the adsorption of a species at the electrode surface or a covalent attachment of redox mediators to the electrode, and (2) modification by a multilayer, which is most frequently achieved by the use of polymeric modifications of the electrode. Here too, specific details of the modification procedures may be crucial to the development of useful biosensing devices.

Mediators are also frequently used in the final biosensing device. Due to the inaccessible nature of the redox centers of oxido-reductase enzymes, mediators or electron shuttles are added to biosensors either by physically admixing the mediator with the enzyme or by chemically binding the mediator to the enzyme to enhance electron transfer from a reactant or desired analyte through the enzyme to the electrode. For example, mediated glucose sensors involving electron acceptors, such as ferricyanide, quinones, and various organic dyes have been utilized.

The goal of a particular biosensing device is to accurately measure a specific biological substrate or analyte within a sample solution. For example, a reliable fructose sensor could be of use for the quantitation of the sugar in food products such as fruit juice, high fructose corn syrup and wine, as well as in clinical samples including blood serum and seminal plasma. Although an enzymatic spectrophotometric assay is available for fructose determination, the assay is time intensive, tedious and costly.

Several groups recently have described the immobilization of Gluconobacter sp. fructose dehydrogenase, a 140 kDa, membrane-bound, pyrroloquinoline quinone-containing oxidoreductase, or various electrodes to give potential fructose biosensors. This fructose sensing enzyme has also been immobilized on glassy carbon, gold and platinum by entrapping it in conductive polypyrrole matrices on platinum and coupling it with the organic conducting salt TTF-TCNQ in a polypyrrole matrix on glassy carbon. Alternatively, the enzyme has been secured on a carbon paste electrode with and without mediators. This fructose sensing enzyme also has been immobilized within a cell-membrane mimetic environment on gold in the presence of a mediator. While these approaches delivered some promising results, readily oxidizable inteferents such as ascorbic acid in citrus juice were found to overwhelm the fructose signal. When this problem is partially avoided by using lower redox potentials, relatively poor sensitivity and low current response is the result.

Other biological analytes of interest are creatinine, creatine and sarcosine. Creatinine is the final product of creatine metabolism in mammals. During kidney dysfunction or muscle disorder, the creatine concentration in serum/plasma may rise to levels several fold the norm. The measurement of the creatinine levels in serum and the determination of the renal clearance are widely used for laboratory diagnosis of renal and muscular function. Most creatine measurements, however, rely on spectrophotometric procedures based on the Jaffe reaction. These assays are analytically limited in that the Jaffe reaction is not specific for creatinine. Given this, many other substrates interfere with the assay leading to inaccurate determinations of creatine concentration in the sample.

In the case of creatinine biosensors, these sensors were first described by Meyerhoff and Rechnitz in 1976. Since that time, many enzymatic creatine sensor systems have been developed. More recent work on creatinine biosensors has utilized a sequence of three enzymes with sarcosine as the final enzyme which requires oxygen to reoxidize the enzyme. In this example, the presence of creatinine was detected by amperometric measurement of concentration changes of either oxygen consumed, or hydrogen peroxide, formed in the final reaction. These methods, however, are rather complex and inefficient because there is a stringent requirement for precise control of oxygen concentration in the system. It is inconvenient, for example, to ensure that oxygen concentration in a series of blood samples is maintained at a constant. Additionally, the electrodes for hydrogen peroxide detection require high overpotentials which may cause blood metabolites, such as ascorbic acid or uric acid, to be oxidized at the electrodes, thus leading to inaccurate measurements.

In summary, although the prior art teaches the use of amperometric biosensing systems as tools to accurately measure biological analytes of interest, many problems arise in the application of these biosensors, such as the relative sensitivity, selectivity and stability of the sensing device.

In particular, some systems are prone to inaccuracies due to the presence of interfering agents present in the test samples. One example, is the presence of ascorbate in fruit juice. The ascorbate acts an interferent and leads to biosensing devices that are inaccurate in terms of the concentration of the measured analyte. Another problem arises from uncontrolled oxygen concentration in some biosensing systems designed to measure creatinine. Thus, there exists a need for biosensors which are highly selective sensitive, and not prone to interference by other chemicals present in the sample. Finally, it is desired that these biosensors also display increased stability, thus allowing for repeated use of the sensing electrode.

SUMMARY OF INVENTION

The present invention relates to amperometric biosensor electrodes useful for the accurate, reliable and sensitive measurement of an analyte of interest in the environmental, industrial, or clinical setting. In their most generic form, the biosensors of the present invention comprise a metallic electrode upon which a lipophilic layer is deposited via chemisorption. The metallic electrode is further modified via a detergent dialysis protocol wherein a redox active enzyme, capable of binding and reacting with a substrate/analyte, is co-immobilized on the chemisorbed, self-assembled, lipophilic monolayer. Additionally, a mediator, which facilitates electron transfer between the enzyme/substrate complex and the electrode, may be co-immobilized within the lipophilic layer or may be added to the surrounding solution. Also included in the biosensors of the present invention is an amphiphilic layer deposited over the lipophilic monolayer forming a second self-assembled layer. The presence of this amphiphilic layer provides advantages in the final biosensing device in terms of its relative stability, activity, and capacity to reject interferents. Further, the family of biosensors of the present invention also includes a sensor based on a system of enzymes covalently coupled to a chemisorbed thiol via a coupling or crosslinking reagent, and thus indirectly coupled to the electrode.

Metallic electrodes suitable for use in the present invention consist of gold, platinum, palladium and silver. Metallic electrodes which facilitate the chemisorption of the lipophilic layer are preferred. In this embodiment, a gold electrode is preferred as the transducer in the sensor system since thiols chemisorb to gold to give a strong, stably bound layer. Other chemical groups suitable for adsorption to a metal surface include sulfates, sulfonates, phosphates, and selenides. Thiol chemisorption on gold yielding thiolate is preferred, due to the relative stability of the metal-sulfur bond.

In the present invention, the lipophilic layer is preferably chemisorbed onto the metal surface of the electrode forming a self-assembled monolayer (SAM). Preferably, this lipophilic monolayer is formed using alkanethiol, such as octadecyl or dodecyl mercaptans. Additionally, short chain, functionalized disulfides or thiols, such as cystamine dihydrochloride and 3,3'-dithiodipropionic acid, which form $SCH_2CH_2CH_2COO^-$ and $SCH_2CH_2NH_3^+$ on the electrode surface, can be utilized to facilitate electrostatic binding of the sensing enzyme or other enzymes. Thus, one purpose for the deposition of the self-assembled, lipophilic monolayer in the present invention is to provide a suitable medium for the immobilization of the enzyme and other components, such as mediators and/or coenzymes.

The enzyme component of the present biosensor is preferably chosen from the group of membrane-bound or lipophilic redox enzymes. The enzyme is preferably selected for its ability to specifically bind to and react with a substrate/analyte of interest. A preferred embodiment of the present invention comprises D-fructose dehydrogenase (FDH), preferably from Gluconobacter species, immobilized on a gold electrode with D-fructose being the measured substrate/analyte. In this embodiment, preferably a co-enzyme, or mediator, is also co-immobilized on the metallic surface with ubiquinone-6 being the preferred mediator for use in the fructose dehydrogenase biosensor. Another embodiment of the present biosensor invention features sarcosine dehydrogenase as the sensing enzyme. In this embodiment, two additional enzymes, creatine amidinohydrolase alone or creatine amidinohydrolase and creatinine amidohydrolase, are also co-immobilized within the self-assembled thiolate monolayer chemisorbed to the electrode surface. In addition, these three enzymes, which are involved in the metabolic pathway of converting creatinine to sarcosine, may be covalently cross-linked to the electrode surface via previously chemisorbed cystamine dihydrochloride to further stabilize the enzyme's co-immobilization or configuration within the lipophilic monolayer. Significantly, this family of covalently modified biosensors can be deposited onto a clean metallic electrode, preferably gold, or a carbon electrode, preferably a glassy carbon electrode in the absence of thiols or lipids. Mediators, such as phenazine methosulfate, 2,6-dichlorophenol indophenol, thionine, toluidine, potassium ferricyanate, and 1,4-naphthoquinone, may also be utilized in this three enzyme embodiment.

Finally, an amphiphilic lipid is a preferred component of the final biosensor electrode. This amphiphilic lipid forms the second self-assembled layer relative to the thiolate monolayer and serves several important functions in optimizing the sensing electrode. The amphiphilic lipid, which is preferably a phospholipid, stabilizes the enzyme and/or coenzyme within the hydrophobic layer. Further, in terms of the fructose dehydrogenase biosensor, the addition of a phospholipid results in near complete rejection of interfacing ions, such as ascorbate. In this particular biosensor, the preferred phopholipids comprise a mixture of dioleoyl-L-phosphatidylethanolamine and dioleoyl-L-phosphatidylcholine. In this regard, both natural and synthetic phospholipids are preferred for use in the present invention, however, two-tailed quaternary amine surfactants and two-tailed surfactants based on benzene sulfonate as the polar headgroup may also be utilized.

Another aspect of the present biosensor invention relates to the method of producing the sensing electrode. The steps in this process include (1) modifying the metallic electrode with thiols whereby the thiols are chemisorbed onto the electrode surface, (2) adding a solution containing an amphiphilic lipid, with or without a mediator, with the amphiphilic lipid preferably being a phospholipid, (3) adding a solution containing at least one enzyme in the presence of a detergent to the solution containing the amphiphilic lipid, and (4) dialyzing the solution containing these components against a buffer until the enzyme and the amphiphilic lipid are co-immobilized onto the electrode surface. Further, the co-immboilized enzymes can be covalently modified wherein the enzymes are linked to each other and/or the surface of the electrode, either directly or indirectly.

Another aspect of the invention includes a method of producing a sensing electrode using covalently modified enzymes, such as those described above for the family of sarcosine dehydrogenase biosensors. In this embodiment, no thiols are required to be chemiadsorbed to the electrode surface. The sensing electrode can be prepared with or without thiols, and the electrode surface also need not be metallic. A non-metallic electrode that may be utilized with the sarscosine family of biosensors is a glassy carbon electrode.

In still another aspect of the present invention, the biosensor electrode is contained within a miniaturized device to further facilitate sample quantification. This amperometric microbiosensor comprises several components. First, a metal wire with a working end to be further electroplated with a noble metal serves as the working electrode, which is prepared by the methods given herein. This biosensing electrode forms the working electrode about which an encasement is then drawn. The working electrode within the encasement is further drawn to a tip of about 1–20 µm in diameter. A Ag/AgCl wire is then inserted into the encasement wherein the Ag/AgCl wire serves both as a reference and counter electrode. Finally, an electrolyte filler is inserted into the encasement to complete the microbiosensor.

The description of the present invention, detailed herein, includes other objects, advantages and features which upon examination of the specification and the accompanying claims will be apparent to those skilled in the art.

DETAILED DESCRIPTION OF THE PREFERRED EMBODIMENTS

Figure 1:
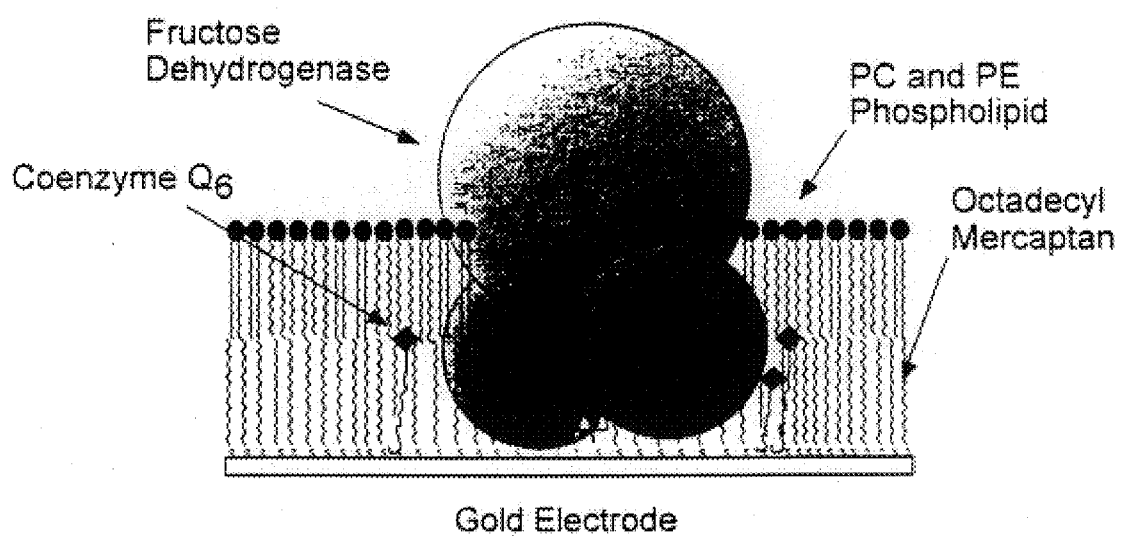
FIG. 1 illustrates a model of fructose dehydrogenase embedded with coenzyme Q in the cell membrane-like layer on a metallic electrode.

The present invention includes a suite of biosensors capable of quantifying the concentration of analytes of biomedical, agricultural, and environmental interest. Analytes of interest include fructose, creatine, creatinine and sarcosine. The novel biosensors of the present invention incorporate conceptual features of the fructose biosensor described in detail herein. Thus, the technology of the present invention is generic allowing for a number of membrane-bound or lipophilic redox enzymes to be incorporated to yield similar biosensors that are of interest to the agriculture and food industries, as well as being useful in the clinical setting.

The novel technology relates to amperometric biosensors based on the immobilization of membrane-bound or lipophilic redox enzymes, such as dehydrogenases or oxidases, in cell membrane-like layers on metallic electrodes. A preferred embodiment comprises fructose dehydrogenase immobilized within a cell-membrane mimetic environment. Still another preferred embodiment comprises a trio of enzymes, namely sarcosine dehydrogenase, creatinine amidohydrolase and creatine amidinolydrolase, also immobilized within a cell-membrane mimetic environment. In this embodiment, however, crosslinking of the system of enzymes to the electrode is preferred due to the increased in stability/activity of the resultant sensor. Preferably, the novel biosensors are assembled on a gold electrode, although the use of platinum, palladium and silver metallic electrodes are also be suitable for use in the present invention.

Membrane-bound or lipophilic redox enzymes, such as fructose dehydrogenase and sarcosine dehydrogenase, are water insoluble biocatalysts that normally exist in association with the hydrophobic part of cell membranes. The basic structural unit of a cell membrane is a phospholipid bilayer. In the present invention, a first lipid layer on a gold electrode is created using chemisorbed thiols that resembles components of a cell membrane. This hydrophobic monolayer provides a stable medium for the immobilization of membrane-bound redox enzymes. In some cases, direct electron transfer is achieved between the enzyme redox centers and the underlying electrode. In most instances, however, the addition of an electron shuttle, or an electron transfer mediator, such as a quinone or an organic dye, is required.

The present invention relates to biosensors that can accurately, reliably and sensitively measure the concentration of analytes in a sample solution, in particular, fructose, creatine, creatinine and sarcosine. The invention also includes solutions to certain problems inherent to the construction of accurate and reliable biosensors. A common problem associated with biosensing devices leading to inaccurate measurements is the presence of interferents in the sample solution. For example, although some progress has been made in the development of suitable fructose biosensors, readily oxidazable interferents, such as ascorbic acid in citrus juice have been found to overwhelm the fructose signal. The quantification of creatinine, for example, in solution is also fraught with problem from interferents.

The biosensors of the present invention further seek to solve the problems of interferents by the immobilization of a membrane-bound enzyme in a lipophilic, and/or amphiphilic self-assembled layers on a metallic electrode, preferably a gold electrode. The biosensors of the present invention also preferably comprise two such self-assembled layers. One layer is comprised of alkanethiols chemisorbed to the electrode. Alkanthiols, such as octadecyl mercaptan, chemisorb quite readily to gold, for example, to form well-ordered densely packed monolayers. In addition to providing a membrane-like environment for the enzyme, these hydrophobic layers can reduce access of polar electroactive species to the electrode surface, thus decreasing the signal from these interferents. Furthermore, an alkanethiolate layer has the advantage of effectively blocking all, not just anionic, electroactive polar species from non-specific interaction at the electrode surface.

In addition, the present invention includes biosensors comprising an amphiphilic layer, preferably comprising phospholipids, which forms a second layer in these cell-membrane mimetic systems. It is noteworthy that for a fructose biosensor of the present invention, the addition of a mixed layer of phopholipids results in the unexpected advantage of near complete rejection of interferents, such as ascorbate ions.

The present invention also seeks to improve the stability, or lifetime, of the sensing electrode. Various methodologies are utilized to increase the stability of the membrane mimetic on a metallic electrode. For example, in the fructose biosensor, the addition of phospholipid to the system greatly increases the useful lifetime of the electrode. On the other hand, in the development of the creatinine biosensor, the covalent coupling of the array of enzymes to each other, and indirectly to the electrode surface via the chemisorbed thiolates, greatly enhances the stability of the biosensing electrode. Moreover, in these particular biosensor systems, the addition of a ampholipid, preferably a phospholipid, increases both the relative range of activity and stability of the enzyme complexes.

Finally, given the advantages observed in the presence of an amphiphilic layer, in particular a phospholipid layer, the biosensors of the present invention are preferentially constructed via the deposition of an amphiphilic layer over the self-assembled thiol monolayer. This step is included in a detergent dialysis protocol for immobilization of the enzymes detailed herein. Preferably, this amphiphilic layer comprises phospholipids. Although it is known that the addition of phospholipids to a membrane-bound enzyme preparation in solution often results in improved stability and activity of the enzyme, it was discovered that the addition of phospholipids to the surface immobilized systems of the present invention improves not only the stability and activity of the enzyme, but importantly also improves the selectivity of the resultant biosensors. Significantly, the addition of phospholipids increased biosensor lifetimes from hours to months. In the case of the fructose, for example, a large portion of the stability enhancement is due to improved retention of coenzyme, and is not simply the result of the increased enzyme stability. Moreover, for the fructose biosensor, a 2-3 fold improvement in selectivity, assessed as ascorbate rejection, and an approximate 4-fold improvement in activity, measured as an increase in current density at 10 mM fructose, were observed when phospholipids were added to the final biosensor.

I. The Fructose Biosensor

An aspect of the present invention relates to an amperometric biosensor electrode and device that accurately measures the quantity of fructose in a sample solution. This practical fructose biosensor is useful for monitoring and controlling food and beverage manufacturing processes including those for fruit and vegetable juices, honey, high fructose corn syrup, and wine. This amperometric fructose sensor is based on the non-covalent immobilization of fructose dehydrogenase in a self-assembled, cell-membrane-like layers on a gold electrode. The advantages of the system include ease of manufacture (i.e. self assembly), outstanding rejection of electroactive interfering agents, such as ascorbate, improved enzyme stability as compared to other biosensor constructs, and excellent sensitivity, accuracy, detection limits, and response times. Significantly, this novel fructose biosensor is the first to provide near complete rejection of ascorbate, which is a prerequisite for sensor use in the food industries.

Still another aspect of the present invention relates to a method of preparing the biosensing electrode for use in amperometric analysis of fructose concentrations. The electrode is prepared by a novel detergent dialysis procedure which renders the essential components of the sensor immobilized on the electrode in an active and stable form, and also leads to the near complete rejection of ascorbate ions.

Additionally, the current response of the biosensor of the present invention is so sufficiently high that a miniaturized fructose biosensor is developed based on this technology. This microbiosensor, preferably ranging in size from 1–100 $\mu$m, measures samples in the range of 1 $\mu$M to 1 M. A fructose biosensor of this design, however, is preferably miniaturized to the 1–20 $\mu$m range for the convenient non-destructive sampling of individual fruit, or for continuous monitoring of fruit juice, or high fructose corn syrup, production processes. Thus this miniaturized biosensor facilitates the non-destructive analysis of individual fruit and vegetables before and after harvesting. Such a tool is particularly useful to fruit growers concerned about harvest timing in various locations on an orchard, and useful to fruit juice and wine producers in evaluation of raw fruit shipments.

In the present invention, immobilization of the membrane-bound fructose dehydrogenase enzyme in a lipophilic, self-assembled alkanethiolate layer on a gold electrode provides a solution to the problems encountered with prior art amperometric biosensors. These problems include interference by electroactive reagents and overall stability of the sensing system. Alkanethiols, such as octadecyl mercaptan, chemisorb quite readily to gold forming well-ordered, densely packed monolayers. In addition to providing a membrane-like environment for the enzyme, the hydrophobic monolayer can reduce access of polar electroactive interferents (e.g., ascorbate) to the electrode surface.

Electronic coupling of the fructose dehydrogenase enzyme is preferably accomplished through the involvement of a co-immobilized quinone, which shuttles electrons between the enzyme and electrode. In the biosensor of the present invention, the lipophilic electron transfer mediator, ubiquinone-6 (coenzyme Q-6), is preferred as a means to couple FDH to the electrode electronically. In addition to ubiquinone, other lipophilic mediators based on quinones, such as menaquinone, are suitable for use in the present invention. Other chemistries based on well known redox dyes such as dichlorophenol indophenol and phenazine methosulfate are also suitable for use, by, for example, making these dyes lipophilic by the addition of alkyl chains, or by adding thiol groups to the molecule to facilitate chemisorption to the metal electrode.

In the construction of the fructose dehydrogenase biosensor, however, the co-absorption of short-chain, functionalized disulfides (3,3 -dithiodipropionic acid and cystamine dihydrochloride), which form $SCH_2CH_2CH_2COO^-$ and $SCH_2CH_2NH_3^+$ on the electrode surface, is also preferred, along with longer chain thiols, in order to obtain electrostatic binding of the enzyme. In this regrad, virtually any alkanethiol is suitable for use in the present invention to yield the lipophilic portion of the chemisorbed monolayer, however, longer alkanethiols are preferred due to their increased stablity. Also single- or multiple-tailed surfactants with a headgroup are suitable for use with the biosensors of the present invention, such as a phospholipid containing a thiol chemisorbed on the headgroup. Alternate thiol containing absorbates that terminate in charged or polar species at the end exposed to the enzyme and aqueous solution can also be utilized in the present invention. These alternative adsorbates include amines, carboxylic acids and sulfonic acids.

FIG. 1 presents a plausible arrangement on the biosensors of the present invention, wherein the membrane-bound enzyme nestles in pockets of the hydrophobic octadecanethiolate layer formed by domains of the shorter chain modifiers. Data also show that the shorter chain, charged modifiers self assemble into domains separate from octadecanethiolate on gold surfaces. The second, or outer layer, is formed with an amphiphilic lipid, such as a phospholipid, to further stabilze the enzyme and co-enzyme within the hydrophobic, thiolate monolayer.

Figure 2:
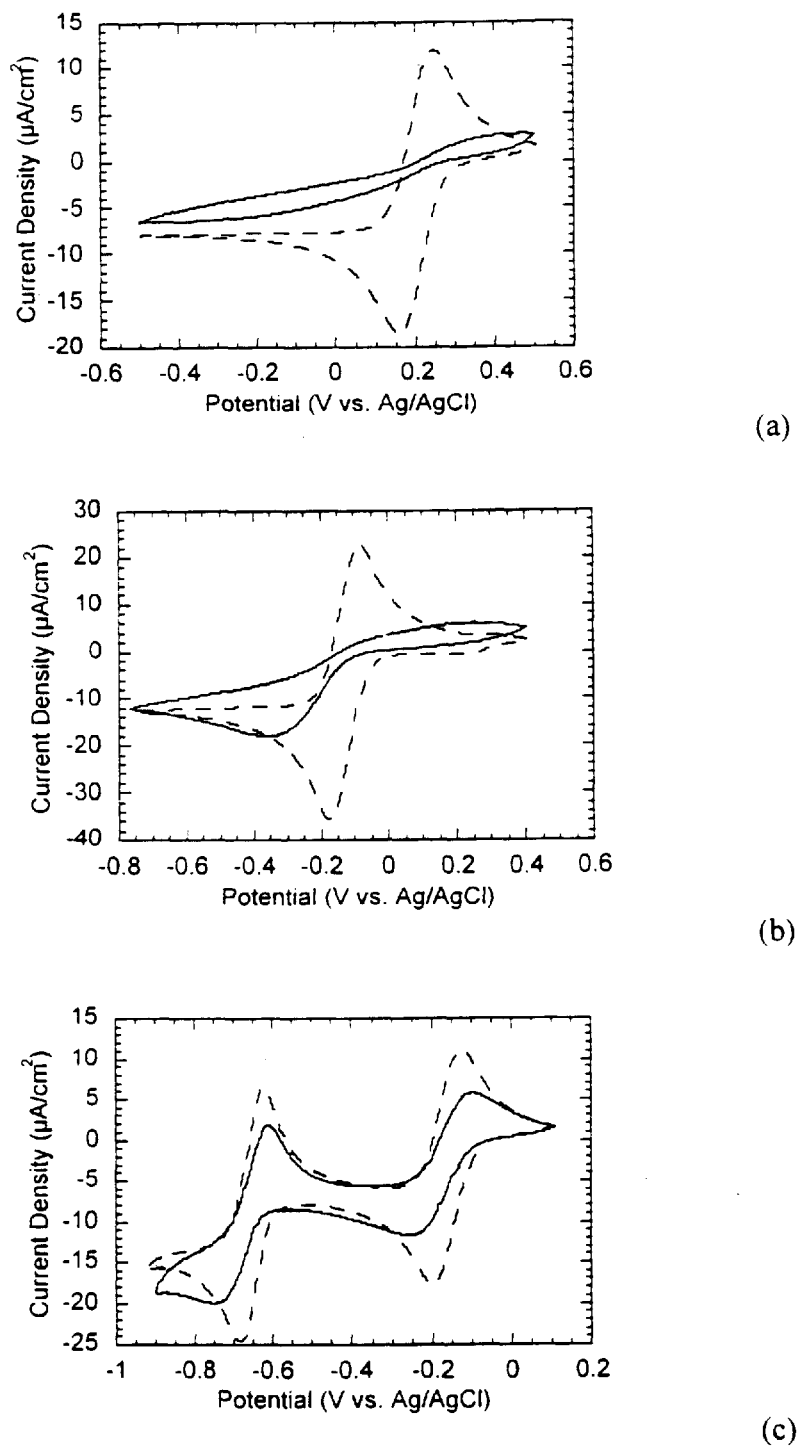
FIG. 2 depicts the steady-state cyclic voltammograms of bare (dashed curves) and phospholipid/thiolate-modified (solid curves) electrodes in solution of 100 mM NaCl and 5 mM (a) $Fe(CN)_6^{3-}$, (b) 1,4-benzoquinone, and (c) methyl viologen and $Ru(NH_3)_6^{3+}$ using a scan rate of 50 mV/s.

In the present invention, the enzyme and coenzyme are immobilized with phospholipids on a modified gold electrode by a simple detergent dialysis procedure. The gold electrode is first modified prior to enzyme immobilization with a mixture of thiols, octadecyl mercaptan and the two shorter-chain, charged thiol species, by self-assembly from an ethanolic solution. As illustrated in FIG. 2, the addition of phospholipids to the enzyme electrode construct not only improves coenzyme retention and enzyme stability, but provides near complete insulation against electroactive interferents, such as ascorbic acid.

Figure 3:
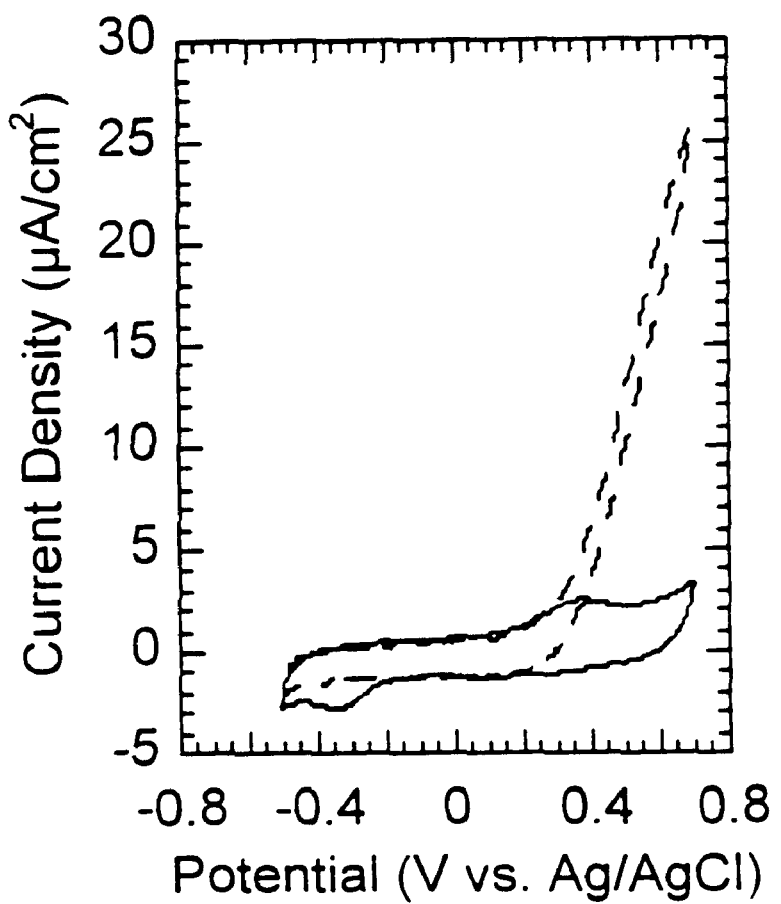
FIG. 3 depicts the steady-state cyclic voltammograms of Q-6/FDH electrode in deoxygenated, 10 mM $KH_2PO_4$ pH 4.5 buffer (solid curve) and with 20 mM fructose added (dashed curve) using a scan rate of 50 mV/s.

When Q-6 and FDH were co-immobilized in the mixed thiolate/phospholipid layer on gold, electroenzymatic activity was demonstrated by comparison of cyclic voltammograms obtained in the absence and presence of fructose, as illustrated in FIG. 3. In buffer alone, only the redox waves of coenzyme Q-6 were visible. However, in the presence of 20 mM fructose, a significant stable catalytic current was observed due to oxidation of fructose by FDH and turnover of coenzyme Q-6 by the electrode. To confirm the role of the enzyme in the catalytic response to fructose, Q-6 was immobilized in a mixed-monolayer electrode without FDH. This electrode did not respond catalytically when exposed to fructose. In additional control experiments, modified electrodes with immobilized FDH and no coenzyme, as well as bare gold electrodes subjected to the enzyme immobilization procedure in the absence of enzyme, did not exhibit Faradaic current in buffer or in the presence of fructose.

Figure 4:
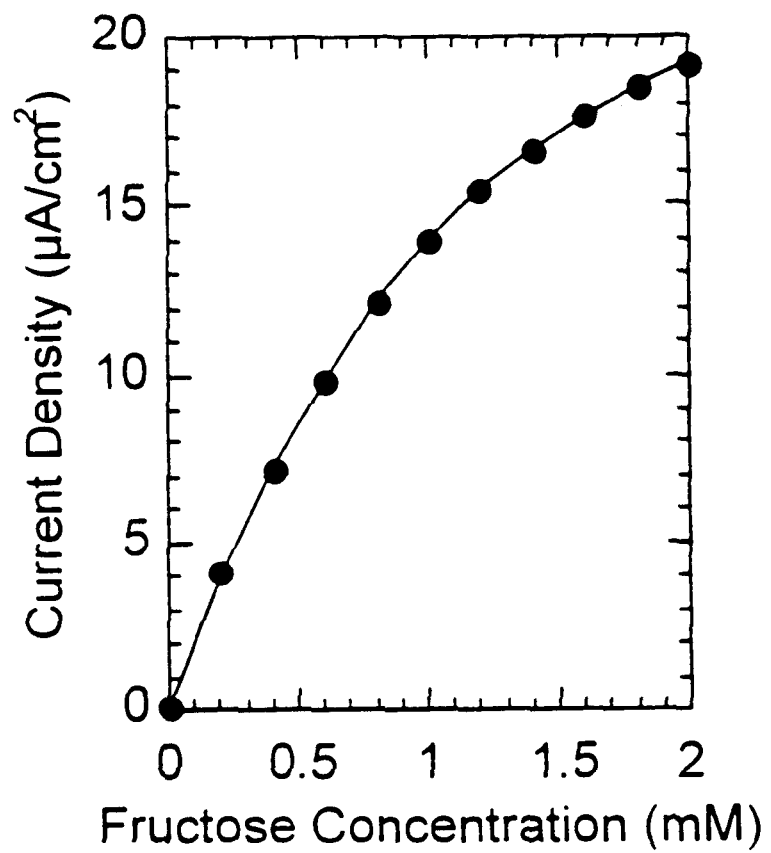
FIG. 4 depicts the calibration curve for D-fructose determined by a Q-6/FDH electrode.

FIG. 4 depicts a typical calibration curve obtained with a Q-6/FDH modified electrode poised at a potential of 0.5 V vs. Ag/AgCl where reoxidation of Q-6 by the electrode is assured. At lower concentrations of fructose, a linear relationship between current and concentration was observed, while the current approaches a saturation value at higher fructose concentrations. This linear range is extended by adding a mass transfer resistance, such as a porous polymeric membrane, over the electrode surface. The typical calibration curve was linear to about 0.5 mM. The sensitivity, or the slope, of the plot in FIG. 4 was 15 $\mu A/cm^2 mM$. Maximum current densities at 10 mM fructose measured as much as 45 $\mu A/cm^2$ for many electrodes. The lowest fructose concentration measured was 10 $\mu M$. However, the detection limit with the 0.02 $cm^2$ electrode is as low as about 250 nanomolar at a current of 1 nanoampere. The preferred concentration range for detection of fructose in the biosensor of the present invention is from about 100 nM to 1 M.

Fructose dehydrogenase is known to be highly specific for fructose. As embedded in the biosensor invention, the Q-6/FDH electrode response was also observed to be highly specific with no current being detected in the presence of glucose. Additionally, galactose, sucrose, lactose, maltose, xylose, arabinose, and sorbitol when added at 1 mM to a 1 mM solution of fructose did not affect the measured current. High sugar selectivity also has been observed for an amperometric fructose sensor based on FDH immobilized on a carbon paste electrode containing benzoquinone, however, this system exhibited the disadvantage of exhibiting a strong, non-specific response to ascorbic acid. The negative results with glucose, galactose and other sugars exhibited by the biosensor of the present invention indicates that the lipid/thiolate layer effectively blocks direct access of sugars to the gold electrode surface and that FDH is highly selective for fructose.

Figure 5:
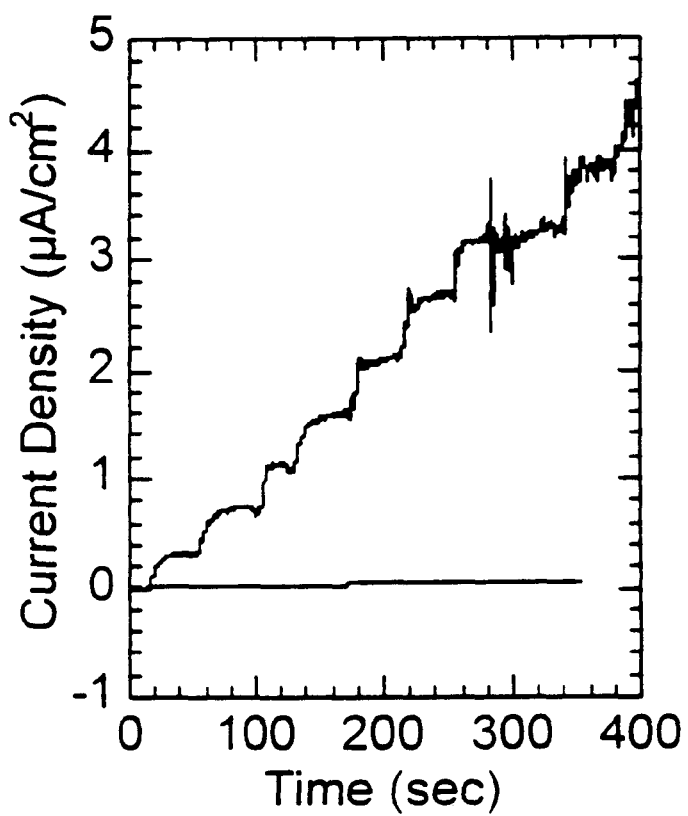
FIG. 5 depicts the current response of a bare (upper curve) and a Q-6/FDH (lower curve) electrode at 0.5 V vs. Ag/AgCl to ascorbic acid from 0 to 1.0 mM added in 0.1 mM increments with magnetic stirring of the solution containing 10 mM $KH_2PO_4$ at a pH 4.5.

Prior to application of an FDH electrode to the measurement of fructose in citrus juice, the effects of electroactive ascorbic acid was evaluated. Ascorbic acid, which is electroactive at oxidizing potentials, is typically present in citrus juice at concentrations 2–3% that of fructose, and its presence can cause amperometric fructose electrodes to give false, high readings. FIG. 5 shows, however, that over a range of 0 to 1 mM ascorbic acid, a gold electrode modified with the membrane-mimetic layer of chemisorbed thiols overlaid with phospholipids showed at least a 60-fold reduction in oxidative current response to ascorbic acid as compared to a bare gold electrode. Also shown in FIG. 5 is the effect of 0.1 mM ascorbic acid on the measured current of a 2 mM fructose solution. In this case, the presence of ascorbic acid at 5% of the fructose level resulted in an error of just 4%. In contrast, it has been reported that ascorbic acid at 2.5% of the fructose concentration results in a positive error of 80% for a sensor based on FDH immobilized on a carbon paste electrode. Thus, the blocking phospholipid/thiolate layers of this system has the unexpected advantage of limiting access of ascorbic acid to the electrode surface. FIG. 5 also shows the effect of ascorbic acid on the same electrode 22 days later. Although the resulting positive error had increased to 9%, this increase in error is likely due to an almost 40% drop in measured current for 2 mM fructose rather than degradation of the blocking phospholipid layer. Given these data, at typical levels of ascorbate, which is generally 2–3% of the fructose concentration in fruit juice, only a relatively small error of 1–5% is expected.

Figure 6:
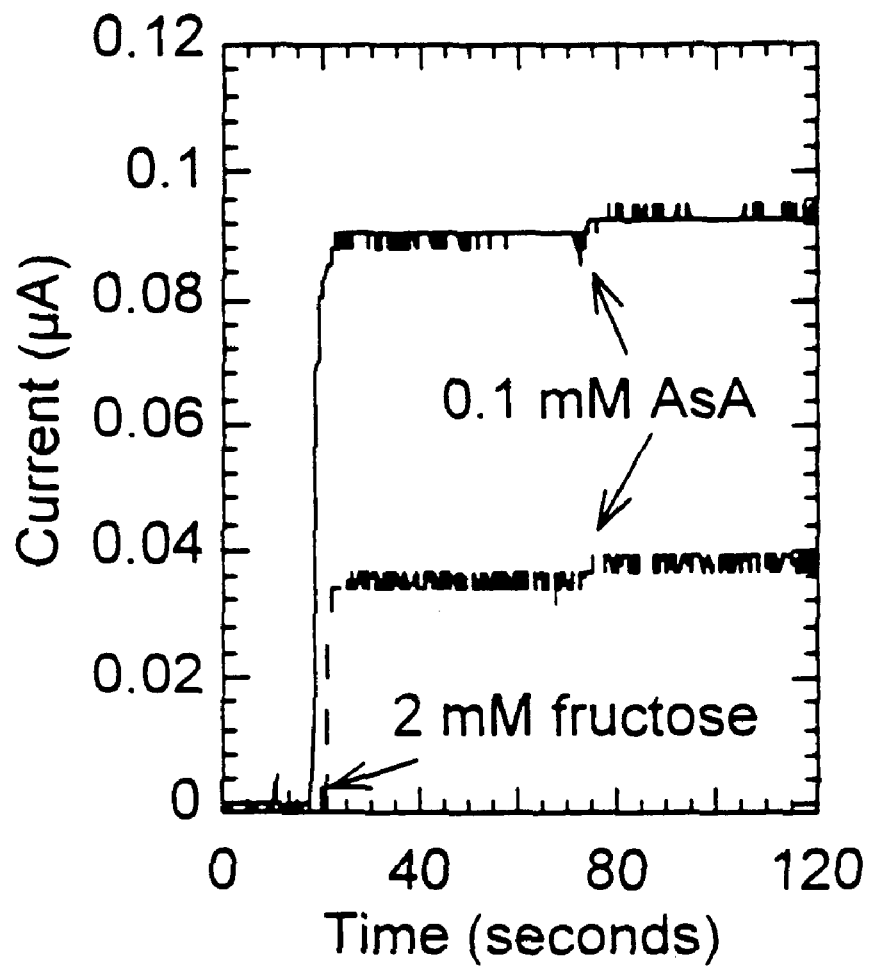
FIG. 6 depicts the response of a Q-6/FDH electrode to injected fructose and absorbic acid over a 28 day period; day six (solid curve) and day twenty-eight (dashed curve). The electrode potential was poised at 0.5 V vs. Ag/AgCl in 10 mM $KH_2PO_4$ buffer at pH 4.5 while the solution was magnetically stirred.

FIG. 6 illustrates the rapid response time of the Q-6/FDH electrode. Upon addition of 2 mM fructose to a stirred phosphate buffer solution, the steady-state current response generally was obtained within about 20 seconds. Within three seconds, the electrode response is within 4% of the steady-state current. Within 11 seconds, the measured current is within 2% of steady state (1.2%). Typical current responses are generally less than 30 seconds for this biosensor. Moreover, this performance equals or surpasses that of earlier FDH-based fructose biosensor prototypes.

The stability of a Q-6/FDH electrode of the present invention was evaluated over a period of six days. The electrode was used daily for many hours and was subjected to repeated rinsing. At the end of each day, the electrode was stored in buffer at 4° C. The calibration curves for the first three days were virtually identical. Sensitivity decreased about 10% on day four and remained unchanged on day five. On the sixth day, sensitivity dropped an additional 8%. This decline in sensitivity could be linked to loss of enzyme activity or leaching of coenzyme from the layer. Earlier FDH immobilization results without phospholipid suggested, however, that the loss of coenzyme is the primary factor, as re-introduction of coenzyme results in improved sensitivity. In previous constructs without the phospholipid layer, significant coenzyme was lost in hours, resulting in an unacceptable sensor lifetime of a day unless the quinone was replenished on the electrode by soaking in a buffer saturated with coenzyme Q. Results with the biosensor of the present invention, however, indicate that the useful lifetime of the electrode co-immobilized within the lipid layer is from about one to six months. Thus, this fructose biosensor, which includes a phospholipid layer, exhibits the unexpected advantage of increasing the useful lifetime of the biosensing electrode.

II. The Sarcosine/Creatine/Creatinine Biosensor

Another aspect of the present invention includes an amperometric biosensor for the clinical assay of creatinine, creatine, and sarcosine contents in human serum and urine. This creatinine biosensor is constructed via the coupling of these related enzymes to a modified or clean electrode surface and correlating the current responses to the concentrations of the analyte or substrate. The three related enzymes configured within the biosensor are sarcosine dehydrogenase, creatinine amidohydrolase, and creatine amidinohydrolase, which are involved in the metabolic pathway of creatinine to sarcosine via creatine and further to glycine.

Figure 7:
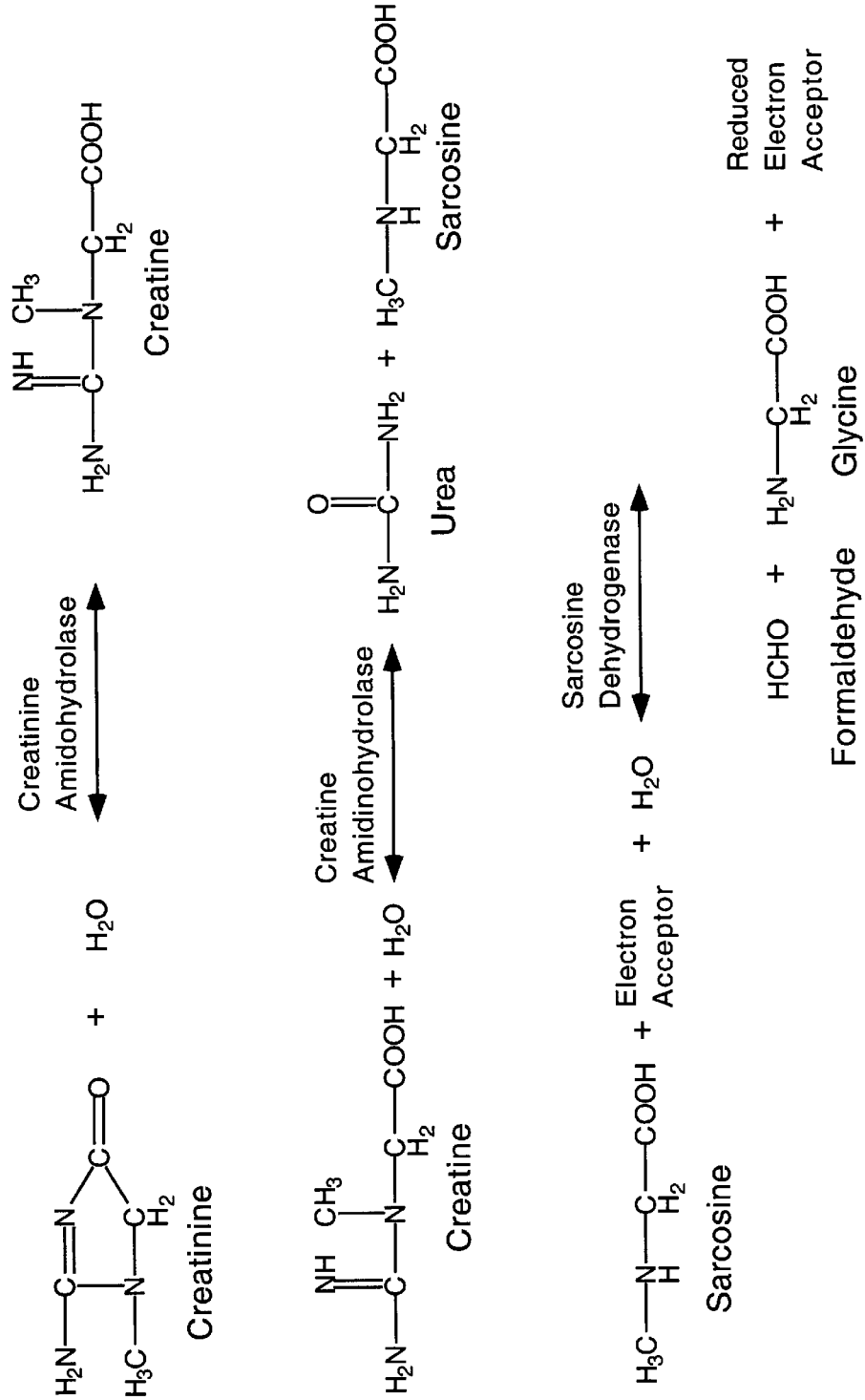
FIG. 7 depicts the reaction pathway for enzymatic determination of creatinine, creatine and sarcosine.

FIG. 7 illustrates the reaction pathways leading to the formation of creatine and sarcosine from creatinine. From this reaction pathway, it is apparent that a biosensor comprising, creatine amindinohydroase, in addition to sarcosine dehydrogenase, is suitable for the measurement of creatine, as well as the less abundant sarcosine, whereas, a biosensor comprising all three enzymes is suitable to measure creatinine, creatine, and sarcosine. Thus, the present inventions includes a family of creatinine-related biosensors. The unifying redox enzyme component in this family of biosensors, however, is sarcosine dehydrogenase.

Importantly, the utilization of sarcosine dehydrogenase in the biosensor construction eliminates the requirement for oxygen because this enzyme can be reoxidized by a variety of synthetic mediators such as phenazine methosulfate, 2,6-dichlorophenol indophenol, thionine, toluidine blue, potassium ferricyanate, and 1,4-haphthoquinone. Therefore, the amperometric detection of sarcosine, creatine, and/or creatine is determined by the reoxidation of any of these synthetic mediators at the electrode at a relatively lower potential. Furthermore, sarcosine dehydrogenase offers the possibilities of co-immobilizing both the enzymes and the mediator on the electrode surface.

The present invention also includes the development of various immobilization techniques for these enzymes and its mediator on the modified electrode, as well as methods of optimizing the stability and responses of the multi-enzyme biosensors. Thus, the invention also includes optimizing the hydrophobic and/or covalent interactions required for immobilization of the enzyme sarcosine dehydrogenase, or the other relevant enzymes in the creatinine pathway, to a gold electrode surface modified with different length alkyl chains. Preferentially, these alkyl chains are selected from a mixture of octadecyl mercaptan and cystamine dihydrochloride, and preferably in a 2:3 ratio of mercaptan to cystamine, although ratios of .5:1 to 5:1 are suitable for use in the present invention.

Figure 8:
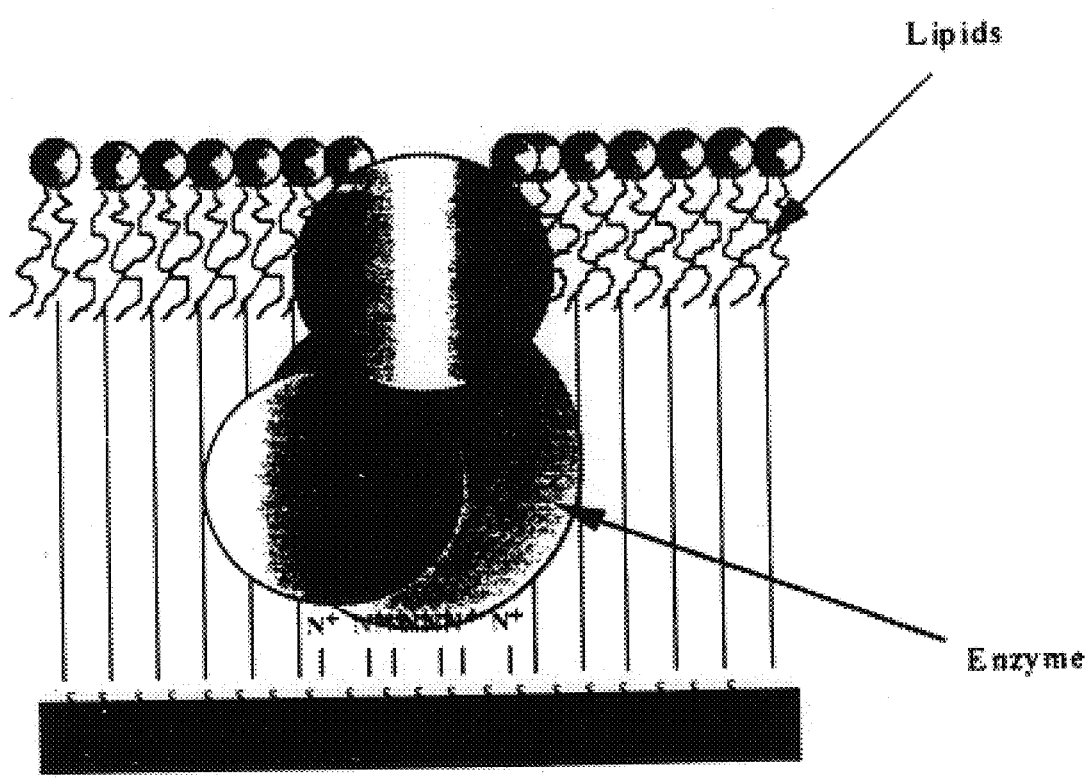
FIG. 8 illustrates a schematic of the creatinine biosensor depicting sarcosine dehydrogenase immobilized in a pocket of hydrophobic self-assembled monolayer on a metallic electrode.

FIG. 8 illustrates a model of the sarcosine dehydrogenase immobilized in pockets of hydrophobic self-assembled monolayer on a gold electrode or glassy carbon electrode. The model reflects that the varied length of alkyl chains formed defects in the self-assembled monolayer on the gold surface to provide a very stable environment for the enzyme to interact and fixate itself upon the electrode.

Figure 9:
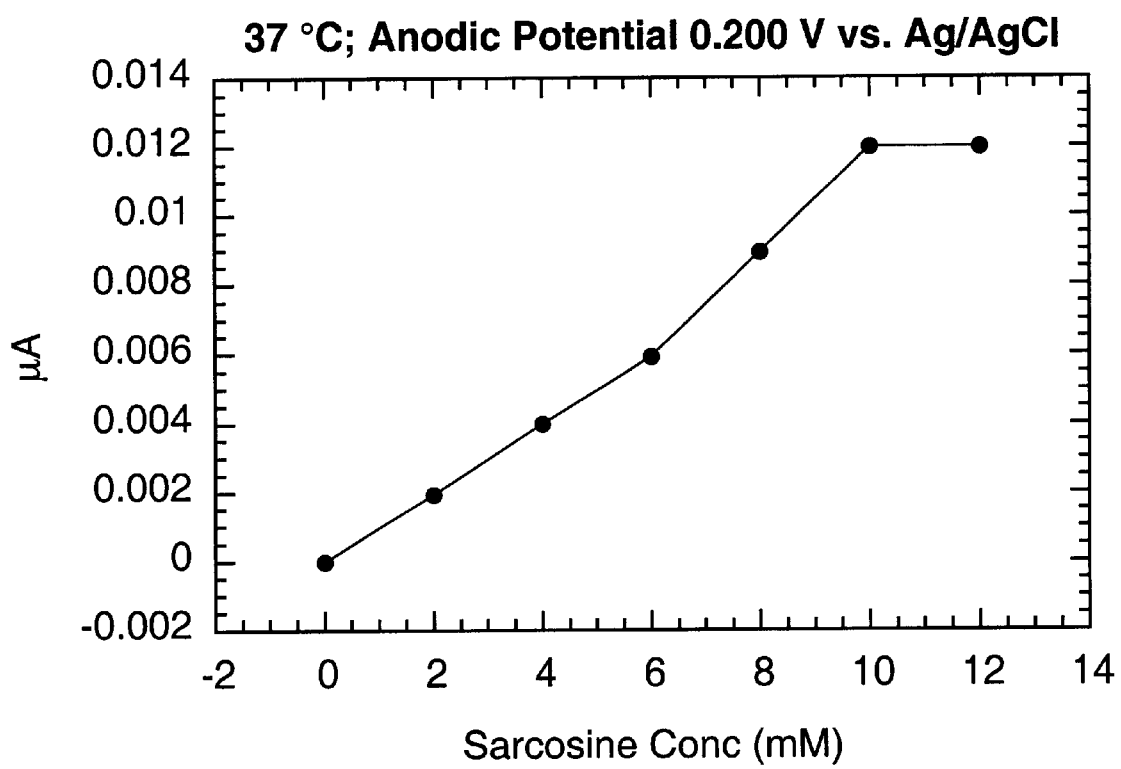
FIG. 9 depicts the current response to sarcosine concentrations using hydrophobic immobilization of the enzyme on a self-assembled monolayer (SAM) electrode in 0.08 mM PMS and 10 mM phosphate buffer, pH 7.5.

As illustrated in FIG. 9, the results using this system confirmed activity of immobilized enzyme with discernible amperometric responses to varying substrate concentrations. The synthetic redox dye phenazine methosulfate was chosen for its favorable kinetics, and it is simply added to solution in this system. Since commercially prepared sarcosine dehydrogenase exhibits relatively low activity, as well as the relatively low stability, the overall content of lipids was increased in order to overcome these inherent problems. In this biosensor, a phospholipid, namely dimyristoylphosphatidylcholine, is preferred. The increased presence of phospholipids in this enzyme mimetic layer was found to improve enzyme activity and stability of the sensing electrode.

Further, it was discovered that although increasing the phospholipid content did increase the enzymatic activity, the biosensor was still unable to retain most of its activity after storage in buffer solution. As a consequence, other enzyme immobilization techniques were utilized for greater enzyme loading and higher enzyme stability/activity. In this regard, covalent cross-linking of sarcosine dehydrogenase, as well as other enzymes in the creatinine designed by Katz et al. where a bifunctional cross-linking agent stilbene-(4,4'-diisothiocyanate)-2,2'-disulfonic acid (DIDS) was applied to covalently link proteins onto electrode surfaces via the thiolate layer. The effect was to build a multi-layer enzyme network to produce relatively strong amperometric responses to varying substrate concentrations. Another method of cross-linking sarcosine dehydrogenase and creatine amidinohydrolase to a glassy carbon electrode or to a gold electrode that may or may not have been previously modified with cystamine dihydrochloride, involves the use of gluraraldehyde as the cross-linking agent and yields a biosensor for creatine. Glutaraldehyde crosslinks the enzymes to one another and may covalently couple them to a modified gold electrode as well. For example, to an enzyme solution consisting of 1 mg/ml of each enzyme, 1 mg/ml bovine serum albumin (BSA), 2 mM EDTA, and 100 mM phosphate (pH 7.5) glutaraldehyde is added to a concentration of 1% by weight of the total protein in solution. Approximately 10 ml of this solution immediately is pipetted onto the surface of a 1.6 mm dia. gold electrode modified with chemisorbed cystamine dihydrochloride as above and allowed to react for 1 hour at room temperature. The electrode than is soaked in 100 mM phosphate buffer (pH7.5) with 2 mM EDTA for 30 minutes prior to first use.

Essentially, the sarcosine dehydrogenase cross-linking protocol described above using DIDS involves a repetition of the following steps, as described by Riklin and Willner.:

1.) Modifying the gold electrodes with cystamine dihydrochloride by soaking in a 10 mM aqueous solution for 2 hours;
2.) Rinsing twice with water;
3.) Immersing the modified electrodes in 20 mM DIDS solution (0° C.) for 10 minutes (100 mM phosphate buffer, pH 7.5);
4.) Immersing the "activated" electrodes in 3 mg/mL enzyme solution (10 mM phosphate buffer, pH 7.2) for 30 minutes. To build the desired layers of enzyme structure, steps 2–3 are repeated. For the final step 4, the reaction was allowed to proceed for up to 4–5 hours at room temperature.

The results of this cross-linking procedure yielded strong, stable current responses with varying sarcosine concentrations. This protocol can be successfully applied to the other enzymes in this system or in related biosensors.

Figure 10:
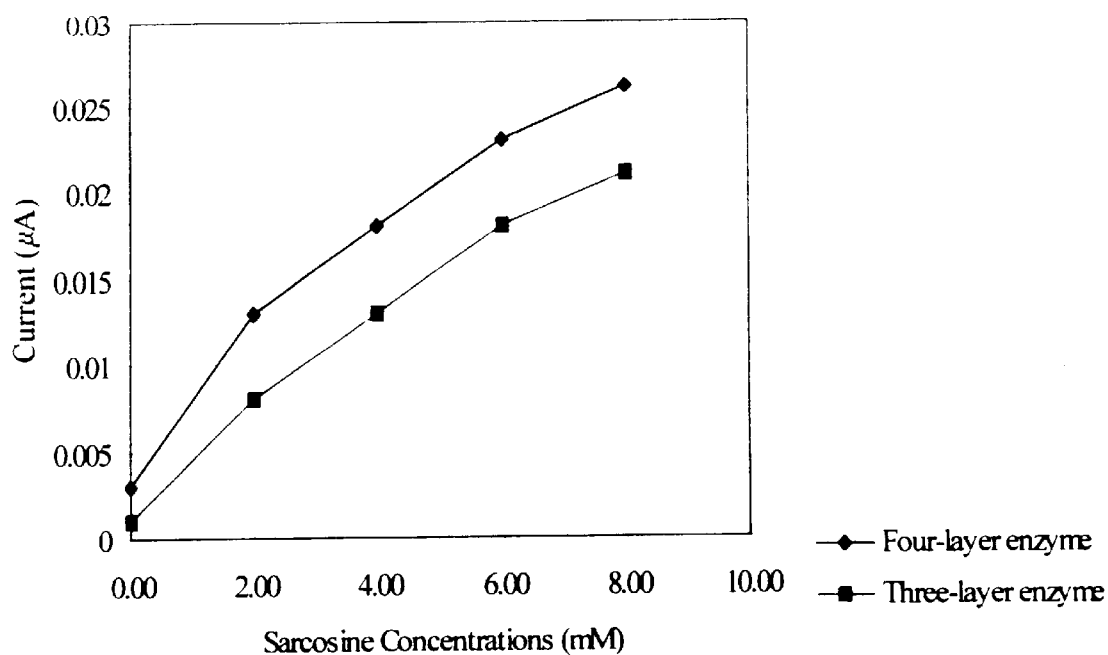
FIG. 10 depicts the current measurements vs. sarcosine concentrations with multilayer enzyme electrodes in 0.200 mM phenazine methosulfate, 100 mM phosphate buffer (pH 7.5) at 37° C.

FIG. 10 shows the current measurements with varying sarcosine concentrations for a three-enzyme layer and four-enzyme layer matrix formed using DIDS. It was apparent that there was higher sensitivity with the four-layer enzyme electrode when the three-layer enzyme electrode and multiple layers beyond four did not produce higher sensitivity. The reason for such may be due to the instability of DIDS cross-linking with higher enzyme layers.

Figure 11:
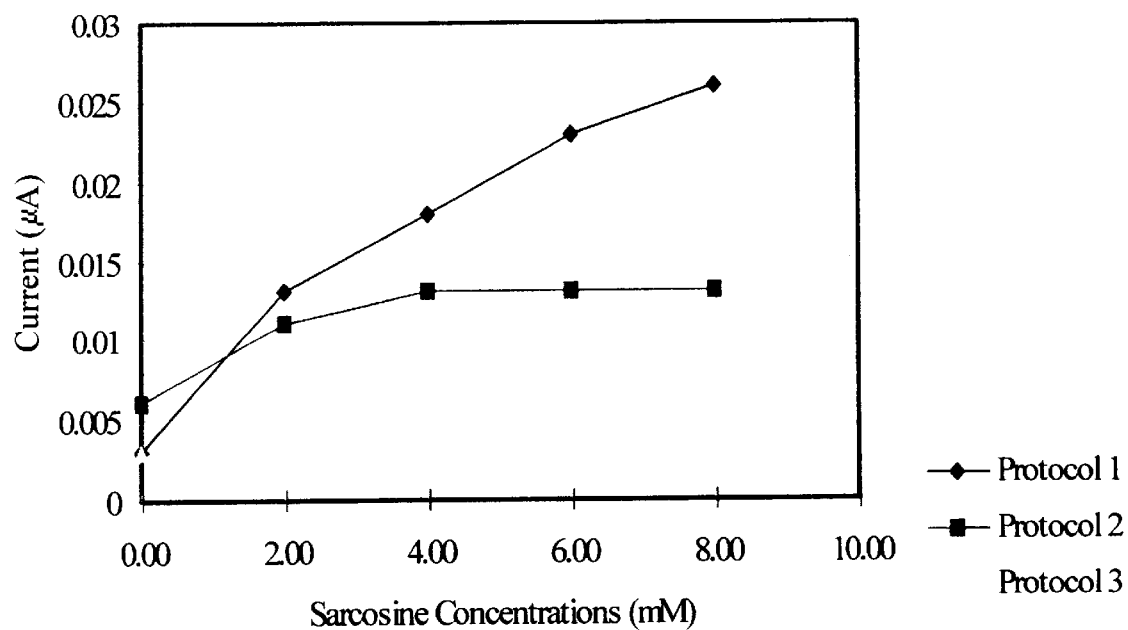
FIG. 11 depicts current measurements of multilayer enzyme electrodes with varied protocols in 0.200 mM phenazine methosulfate, 10 mM phosphate buffer (pH 7.5) at 37° C. Protocol 1: sarcosine dehydrogenase and DIDS; Controls: Protocol 2: sarcosine dehydrogenase only, Protocol 3: DIDS only.

Control experiments were performed to confirm covalent coupling of the enzyme to the modified electrode, as opposed to simple protein absorption. FIG. 11 shows the results of the variations in preparation of these enzyme electrodes. One of the modified electrodes was immobilized using the described protocol to produce a four-layer enzyme matrix, while another one was immersed in only enzyme solution (w/o DIDS), and the last one was immersed in only DIDS solution. Since the electrode that was treated with both DIDS and enzyme solution yielded the strongest currents while the others produced very weak or no currents, we may conclude that sarcosine dehydrogenase was indeed covalently attached to the modified surface.

Figure 12:
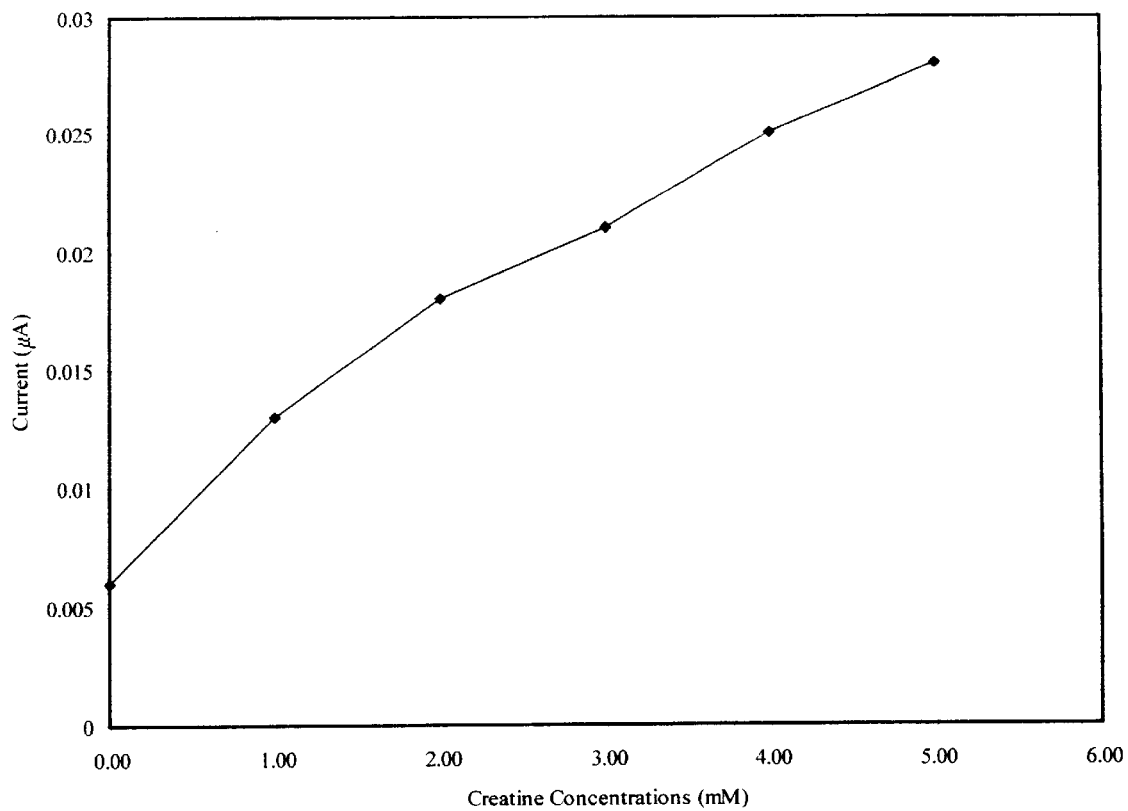
FIG. 12 depicts current measurements of multilayer enzyme electrode with varying creatine concentrations in 100 mM phosphate buffer (pH 7.5) containing 4.59 mg creatine amidinohydrolase and 2.00 mM phenazine methosulfate at 37° C.

We further attempted to co-immobilize both the sarcosine dehydrogenase and creatine amidinohydrolase to the modified electrode surface with this protocol. However, this electrode failed to produce current increases with varying creatine concentrations, while there was still current additions with increasing sarcosine concentrations. Therefore, this protocol failed to effectively couple creatine amidinohydrolase to the modified surface. The reasons may be due to the fact that sarcosine dehydrogenase may possess much more reactive primary amino groups for covalent coupling than does creatine amidinohydrolase, and thus, this immobilization technique may selectively attach one enzyme over another. An additional experiment was performed where a multilayer sarcosine dehydrogenase electrode was used to detect sarcosine produced by creatine amidinohydrolase in aqueous solution. The result shown in FIG. 12, further confirmed effective sarcosine sensing with this immobilization technique.

Since the sarcosine dehydrogenase from the preparation has very modest activity, there is a necessity for high loading capacity of this enzyme on the electrode to yield creatine and creatinine concentration measurements within the sensitive critical range. Chemical aggregation of the enzymes by intermolecular cross-linking effectively immobilize a required volume of the enzymes for this sensing purpose. The first and still most widely used method applies glutaraldehyde as the bifunctional reagent, which establishes intermolecular cross-links at the amino groups of lysine through double bonds of its oligomer. Glutaraldehyde produces stable and insoluble three-dimensional networks of proteins. When glutaraldehyde is applied to solutions of low protein concentrations, it gives rise initially to water-soluble oligomers, but when applied to more concentrated solutions, aggregation rapidly gives rise to high molecular weight, water-insoluble polymers. In order to insolubilize low concentrations of enzyme, it is often necessary to add inert lysine-rich protein, such as bovine serum albumin (BSA), to the enzyme solution. If the concentration of the inert protein is high enough, it can be considered as the insoluble supporting matrix of the enzyme.

Figure 13:
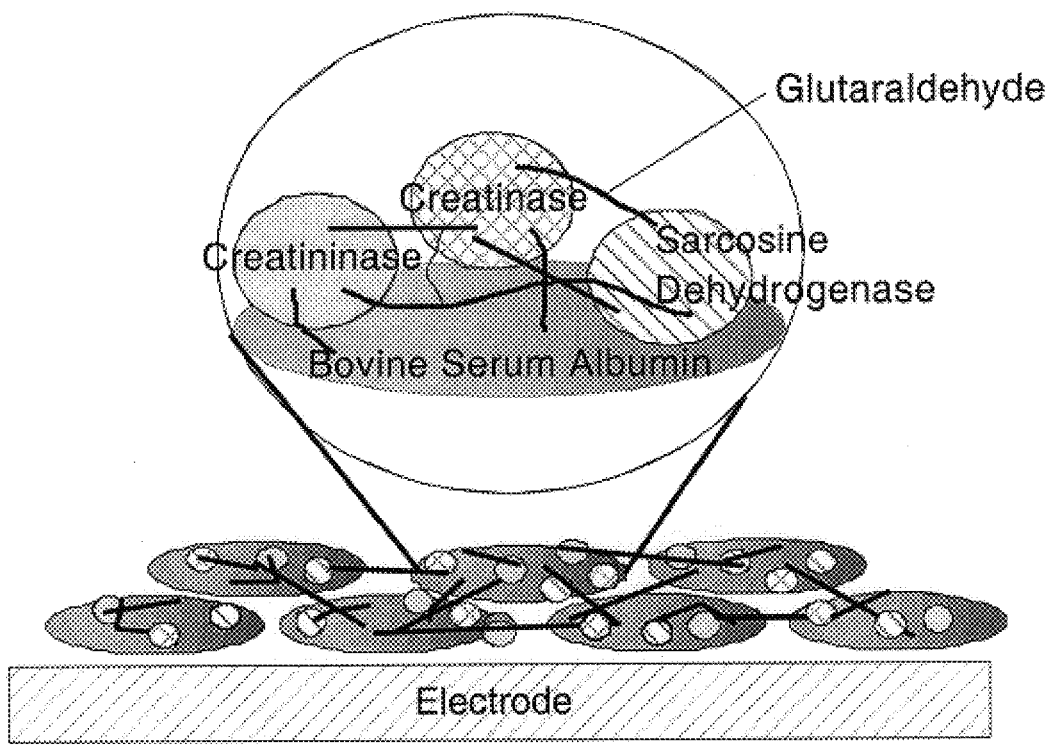
FIG. 13 depicts a representation of cross-linked enzymes absorbed on an electrode surface for a creatinine biosensor.
Figure 14:
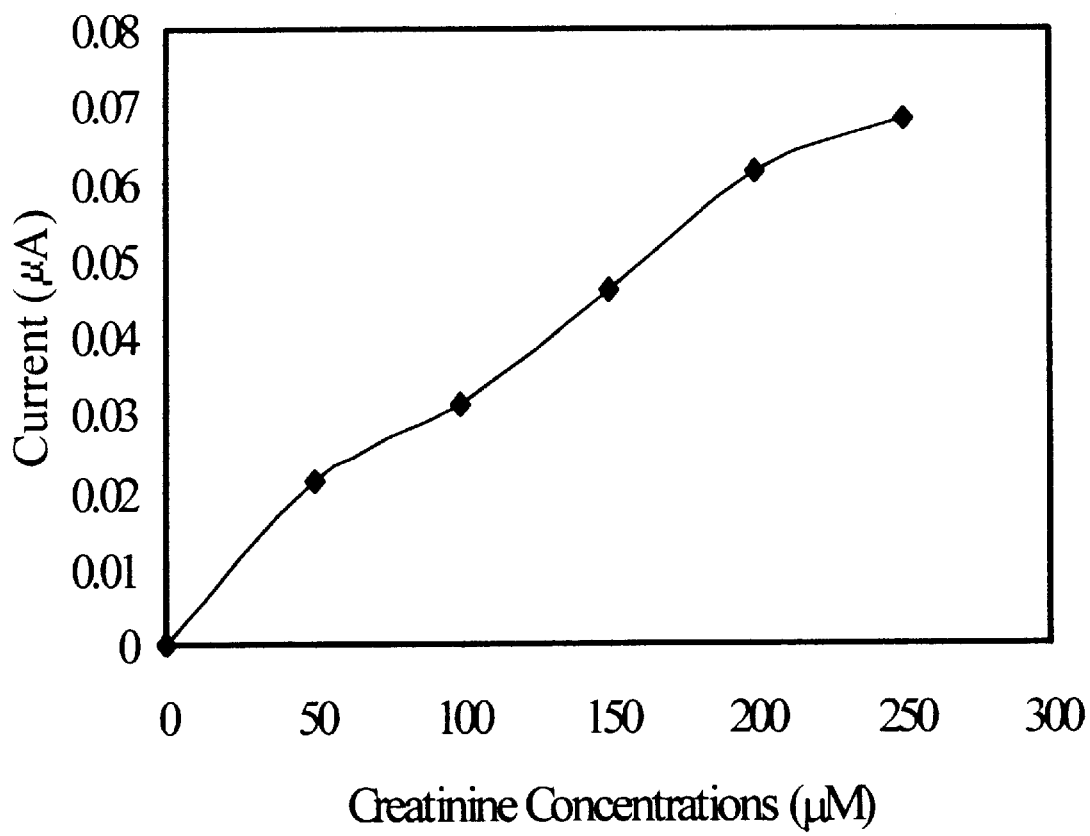
FIG. 14 depicts a calibration curve for creatinine determined by the creatinine biosensor on a glassy, carbon electrode in 100 mM phosphate buffer (pH 7.5) with 0.500 mM 2,6-DCPIP at 37° C.

FIG. 13 shows a schematic representation of the creatinine biosensor featuring three enzyme assays, cross-linked via glutaraldehyde. It is significant that using the glutaraldehyde immobilization technique a thiol layer deposited on the electrode is not required as illustrated in FIG. 13, where a clean gold electrode is utilized. Moreover, using the glutaraldehyde method of cross-linking permits the use of non-metallic electrodes, such as glassy carbon electrodes. FIG. 14 shows a calibration curve for creatinine determined by the creatinine biosensor of the present invention on a glassy carbon electrode.

Aggregation is used to immobilize and thus, retain the enzymes on the surface of the electrode. In this case, the aggregation by glutaraldehyde results in "anchoring" the enzyme polymer into its matrix and the insoluble mass of cross-linked aggregate remains stuck to the electrode surface, as if covalently bound to it. Consequently, since dense binding of the enzymes is required, an aggregation of enzymes by glutaraldehyde on the electrode surface is desirable.

Both the creatine and creatinine sensor prepared in a similar manner displayed effective current outputs to the varying concentrations of creatine and creatinine, respectively. Although a host of synthetic dyes and other reagents functioned effectively as mediators for sarcosine dehydrogenase, only phenazine methosulfate and 2,6-diclorophenol indophenol served as effective mediators for the creatine and creatinine systems.

Finally, these sensors offer possibilities in commercial applications due to their simple, yet more effective features than the currently existing creatine/creatinine sensors. Future work may also explore possibilities of co-immobilizing its mediator on the electrode.

EXAMPLE 1

Biosensor Electrode Modification

A gold electrode was modified for use in the biosensors of the present invention as follows. Monolayer coverage is approximately $4.6 \times 10^{14}$ molecules/cm$^2$ for alkanethiols. Typical modification solutions contain approximately $10^4$ excess thiol for monolayer coverage. The clean gold electrodes are individually modified in 0.5 ml of 1 mM thiol/disulfide ethanol solution which is $10^5$ excess. The disulfides undergo dissociative adsorption at the gold surface and form self-assembled monolayers in much the same way as alkanethiols. Stock solutions of octadecyl mercaptan, the disulfides cystamine dihydrochloride and 3,3'-dithiodipropionic acid are prepared prior to modification. To prepare the octadecyl mercaptan (OM) stock solution, the OM is placed in a water bath on a hot plate set at ~3.5 OM is a waxy solid at room temperature, therefore, heating allows pipetting of OM into ethanol. A 9 mM OM stock solution is used due to the limited solubility of OM in ethanol. When the OM has melted, a disposable micropipette 1–5 μl is used to dispense 3 μl of OM into 1 ml of ethanol contained in a 1 ml volumetric flask/vial. One must work quickly as the OM starts to solidify in the pipette when removed from the bottle. Also, excess OM should be removed from the outside of the pipette. The vial is capped and vortexed. It is also necessary to sonicate the solution to solubilize the OM. Sonication is performed until the solution is clear. Vortexing periodically helps to dispense the OM pellet that forms at the bottom of the vial.

The 10 mM disulfide stocks solutions are prepared by placing the appropriate amount of disulfide in an microfuge tube and adding 1 ml of ethanol to the vial. It is necessary to vortex and sonicate the cystamine solution. The dithiodipropionic solution should be vortexed.

The modification solution is prepared from these stock solutions in appropriate ratios. The various thiol solutions and 0.5 ml of ethanol are pipetted into an Eppendorf vial; the contents are then vortexed. Generally, 40% OM and 30% each of the disulfides were used. However, any any ratio, varied from all mercaptan to all shorter chain thiol, can be utilized in the present invention. Just prior to modification, the clean electrodes are sequentially rinsed with deionized water and ethanol. The electrode is then placed in the microfuge tube. No bubbles should be present at the electrode surface. After the required amount of time has passed (anywhere from one minute to several days with good results being attained with two hour modifications), the electrode is removed and rinsed throughly with ethanol to remove excess thiol. The electrode is then rinsed with and stored in deionized water. Generally, the electrodes were modified on the day that they were used or the evening before.

EXAMPLE 2

Enzyme Immobilization

2a: Immobilization of fructose dehydrogenase and coenzyme in mixed monolayer

The following describes the method of preparing a biosensing electrode in accordance with the present invention.

First dialysis bags are prepared by cutting approximately 2.5 inch lengths of Spectra/Por CE (Cellulose Ester) Membrane 10,000 MWCO tubing (flat width 12 mm) and placing these in deionized water. The dialysis bags are soaked for at least 30 minutes changing the water at least three times. A final soak is does in cold phosphate buffer. The dialysis bags are then stored on ice.

Next a stock solution of FDH is prepared by weighing the appropriate amount of octyl glucoside to give 35 mM or 1% in 1 ml of cold phosphate buffer (10 mM, pH 4.5). FDH is allowed to warm to room temperature before use. 2.5 mg FDH is then transfered via gentle squirting of detergent solution. The stock solution is stored at 4 C between experiments and used within two weeks.

A stock solution of decylubiquinone (DU) or Q-6 is then added to the enzyme detergent solution to yield a 170 M solution. The stock solution is then placed on ice and allowed to equilibrate for at least 30 minutes before it is added to the dialysis bags. Q-6 stock solution is prepared by adding 75 mM octyl glucoside in 1 ml of phosphate buffer to 1 mg of Q-6 producing a stock of 1.7 mM (MW=590.9 g/mol). A DU stock solution is then prepared by adding 190 mM octyl glucoside in 10 ml of phosphate buffer to 54 mg of DU to yield a stock of 17 mM (MW=322.4 g/mol). The DU stock solution is then vortexed and sonicated to disperse the decylubiquinone.

Next a dialysis reservoir is prepared by placing 400 ml of cold 10 mM phosphate buffer pH 4.5. Then ~280 1 of the FDH stock solution is dispensed into dialysis bags along with a modified electrode. Care should be taken to avoid bubbles at the electrode surface. The electrode should be placed so that it is exposed to greatest amount of solution, i.e. just below the surface of the solution.

The electrode in then placed in the prepared reservoir while positioning the electrode/bag so that only the detergent solution is below the reservoir surface. Preferably no more than three electrodes should be used per reservoir. Dialysis should be performed with stirring at 4 C and the dialysate should be changed three to four times over an 18 to 48 hours period.

The final reservoir change should contain the detergent-sorbing resin CALBIOSORB. Approximately 1 ml CALBIOSORB should be pre-rinsed before use and added to a reservoir flask. Next approximately 200 ml of deionized water is used to rinse twice, and then the resin is allowed to settle to the bottom of the flask. Finally, the resin is rinsed with phosphate buffer and added to the reservoir buffer. After dialysis, the electrode is rinsed with deionized water. The electrode can be used immediately or stored in cold buffer, away from light, at 4 C.

2b: Immobilization of fructose dehydrogenase and coenzyme with lipid in mixed monolayer The following is a method to prepare a mixed monolayer biosensor electrode in accordance with the present invention.

Add 100 mg of octyl glucoside (OG) and 300 μl of 1.7 mM coenzyme Q-6 stock solution to yield a final Q-6 concentration 170 μM. The Q-6 stock should be prepared by adding 1 ml of ethanol and then adding approximately 0.5 ml of methanol to dissolve the OG. This is followed by the addition of one ml dioleoyl L-phosphatidylethanolamine (DOPE) and 0.24 ml of dioleoyl L-phosphatidylcholine (DOPC), both 25 mg/ml, to the mixture. The solvent is removed by evaporation at 35 C. Next three ml of cold phosphate buffer (10 mM, pH 4.5) are added. The flask should be placed in the dark to avoid photooxidation of the amphiphiles. The solution is stirred at 4 C overnight. The solution is then filtered, preferably with a Cameo 25NS nylon 1.2 m filter (Micron Separations, Inc.).

Next three mg of FDH is added to the filtered solution, and stirred for 15 minutes. The solution is then allowed to equilibrate for two hours at 4 C. The dialysis bags should be prepared as described in Example 4a, with following exceptions. 300 μl of enzyme solution should be used rather than 280 μl and dialysis is performed for 2–6 days with 4–6 changes in dialysate.

2c: Immobilization of the Creatinine Related Enzymes by Detergent Dialysis

In accordance with the present invention, the immobilization procedure for sarcosine dehydrogenase, and the other related enzymes in the creatinine pathway, generally follows the Examples 2a and 2b described for fructose dehydrogenase as detailed herein.

Overall, the immobilization protocol for the creatinine biosensor involves the following series of steps:

1.) Modify clean gold electrodes with a mixture of varying length alkyl chain thiols as in Example 2a, except that the modification solutions contained Triton X-100 detergent, generally from about 0.01% to 5%.
2.) Immerse the electrodes in 10,000 Molecular Weight Cutoff Dialysis Membranes filled with enzyme-detergent solutions containing 1 mg/ml of each enzyme in order to immobilize the enzyme, and mediators if desired, in the presence (Example 2b) or absence (Example 2a) of phospholipids.
3.) Dialyze away detergent at 4 C with constant stirring for 120 hours.

Example 2d: Forming Multilayers of Immobilized Sarcosine Dehydrogenase Using DIDS The preparation of multilayer enzyme electrodes using 4,4'-diisothiocyanato-trans-stilbene-2,2'-disulfonic acid disodium salt (DIDS) was performed using the technique described by Riklin and Willner. First, the clean gold electrode surface was immersed in a 10 mM cystamine dihydrochloride aqueous solution for 2.0 hours. The monolayer-modified electrodes were then rinsed twice with water and introduced into a cold (0° C.) 100 mM potassium phosphate buffer solution (pH 7.5) that contained 20 mM DIDS for 10 minutes. The resulting electrodes were then rinsed twice with a cold phosphate buffer solution and then soaked in a sarcosine dehydrogenase solution (3.0 mg/ml) for 30 minutes at room temperature. The monolayer enzyme electrode was rinsed with phosphate buffer solution and the two-step procedure using the reaction with DIDS and sarcosine dehydrogenase was repeated to assemble the desired number of enzyme layers on the electrode.

Example 2e: Immobilization of Creatinine Related Enzymes by Glutaraldehyde Cross Linking To prepare a creatine sensor, approximately 1.0 mg creatine amidinohydrolase, 1.0 mg sarcosine denydrogenase, and 1.0 mg bovine serum albumin were dissolved in 120 μl phosphate buffer solution, pH 7.5. 4.0 μl 1.0% glutaraldehyde was added to the enzymes solution and stirred. Approximately 10 μl of the resulting mixture was quickly added to each of the freshly polished and electrochemically cleaned electrodes, using a microsyringe. The enzyme layer obtained was allowed to cross-link in air, at room temperature, for 1.0 hour. The electrodes were then immersed and stored in 100 mM phosphate buffer solution, pH 7.5, at room temperature until further use. To prepare a creatinine sensor, approximately 0.5 mg creatinine amidohydrolase, 1.0 mg creatine amidinohydrolase, 1.0 mg sarcosine dehydrogenase, 1.0 mg bovine serum albumin were dissolved in 120 μl phosphate buffer solution, pH 7.5. The rest of the protocol was accomplished in the same manner as that for the creatine sensor. The electrodes were then immersed and stored in 100 mM phosphate buffer solution, pH 7.5, at room temperature until further use.

EXAMPLE 3

Enzyme Coverage of the Gold Electrode

A method to determine enzyme coverage on the electrode surface was implemented. The plastic Kel-F material surrounding the gold disk was removed; the gold tip was placed in 0.1% Triton X-100 solution and was gently agitated to removed enzyme from the phospholipid/thiolate layer. The solution was then assayed, and the total enzyme activity was compared to that expected for monolayer coverage as estimated assuming spherical enzyme shape. For one electrode, an FDH coverage of 20% of a theoretical monolayer was estimated. Preferred enzyme coverage is from about 20–90%.

EXAMPLE 4

AFM Analysis of the Surface Properties of the Modified Electrode

From the analysis of the modified gold electrode surfaces created in the development of the biosensors of the present invention, it is apparent that standard surface analytical techniques, such as contact angle goniometry and ellipsometry, would not distinguish readily among preparations which displayed significant differences in sensing activity. These techniques provide a macroscopic measure of surface properties that could not capture the finer detail of these heterogeneous electrode surfaces. Thus, atomic force microscopy, a technique which can reveal surface topography, was used to correlate sensing activity with the distribution of the enzyme of the surface of the electrode.

For these AFM studies, atomically smooth gold surfaces were created by evaporating gold onto mica. A glass cover slip then was glued with epoxy to the exposed gold surface and the gold film was peeled from the underlying mica. The side of the gold film originally contacting the mica surface is of the near atomic smoothness required for optimal AFM work.

Figure 15A:
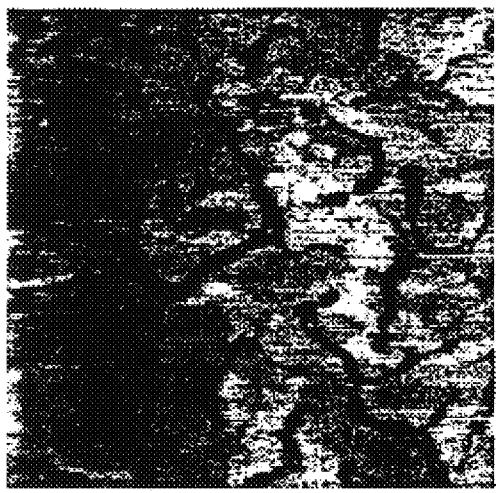
FIG. 15(a) depicts the topographical image of gold with chemisorbed cystamine hydrochloride, 3,3'-dithiodipropionic acid and octadecanethiol with the surface image measuring 1.5 µm on a side.
Figure 15B:
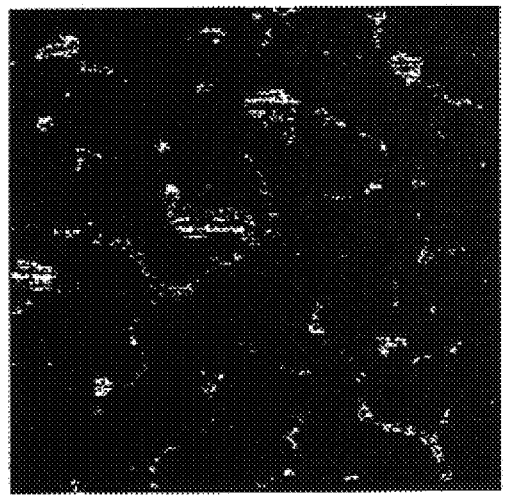
FIG. 15(b) depicts the frictional force image of the same surface in FIG. 13(a).

Both the short and long chain thiols were co-adsorbed on these gold films from ethanolic solution prior to deposition of enzyme and phospholipid by a detergent dialysis protocol. AFM data taken in topographical images, depicted in FIG. 15(a), and lateral force mode, depicted in FIG. 15(b), for the same sample surface reveal the existence of at least two domains on the gold surface. The topographical image indicates the existence of depressed areas on the surface presumably corresponding to domains formed by the shorter chain adsorbates. This view is confirmed by the lateral force image which shows sharp contrast between the same areas on the surface due to their different chemistry and therefore different frictional force on the AFM tip. From the AFM studies, the enzyme, for example FDH, was seen to absorb with nearly equal affinity to all areas of the surface. Further, AFM studies conducted after exposing films to dilute enzyme solution revealed nearly continuous surface films of protein.

EXAMPLE 5

Sensing Activity in the Presence of Short and Long Chain Modifiers

The preferred performance of the biosensors of the present invention, detailed herein, in terms of activity was achieved with a gold surface modified with both the short- and long-chain modifiers. For example, when the gold electrode is modified with just octadecyl mercaptan or just the short-chain thiols prior fructose dehydrogenase immobilization, cyclic voltammograms show a weaker current response to fructose, as compared to the mixed surface system. The ubiquinone mediator, however, is active on all modified surface types investigated. This behavior of the biosensing electrode can be attributed to the enzyme adsorbing to different sites on the surface in different orientations having different activity and/or different access to the electron transfer mediator, ubiquinone. Since the shorter chain thiols do chemisorb into separate domains, it appears that the enzyme nestles in pockets formed by these adsorbates and that sensor activity can be modified by changing the size, shape and concentration of these domains on the gold electrode surface.

EXAMPLE 6

Modified Electrode In the Absence of a Mediator

Figure 16:
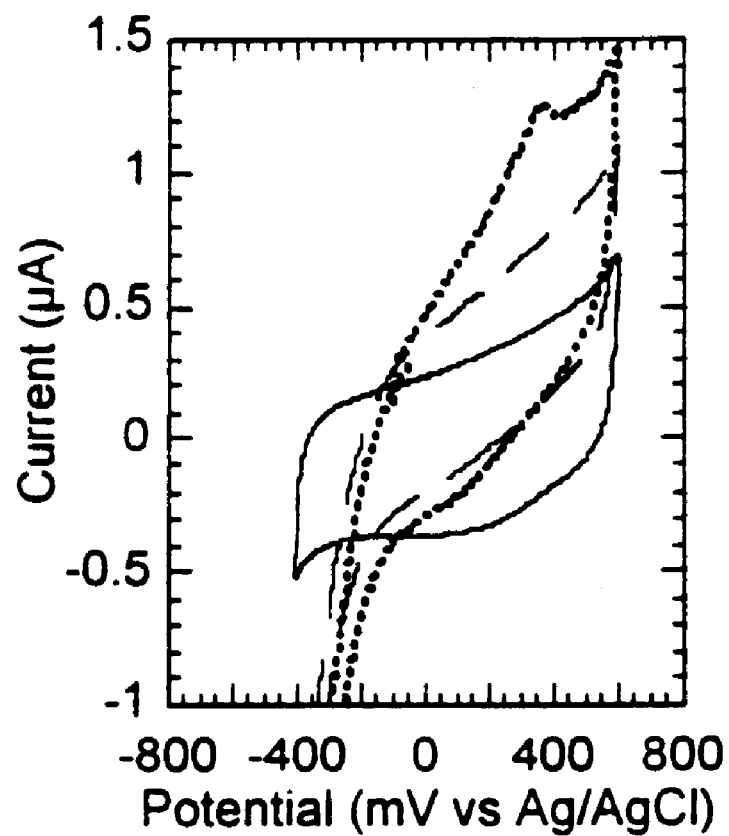
FIG. 16 depicts the steady-state cyclic voltammogram (CV) of FDH in mixed SAM on gold foil in the absence of a mediator in a buffer (solid curve) and CV's in the presence of 10 mM fructose: first scan (short dashes) and scan after seven minutes (long dashes). The CV's were conducted at room temperature in 10 mM $KH_2PO_4$ at pH 4.5.

Further engineering of the gold electrode surface produces a system where direct electron transfer is achieved between electrode and enzyme. The wide separation between current peaks observed for the ubiquinone on our gold surfaces is indicative of sluggish, electrochemically irreversible electron transfer kinetics between mediator and electrode. Elimination of the mediator yields a simpler system having improved kinetics, i.e., response time. The positive cyclic voltammetry results presented in FIG. 16 were achieved using a strip of gold foil with 75-fold greater surface area than the usual 0.02 cm$^2$ gold disk electrodes. As shown in FIG. 16 for the exemplary fructose biosensor, in the absence of any electron transfer mediator, a strong steady-state current response is observed in the presence of fructose which indicates that electrons are transferred directly from the catalytically active enzyme to the gold foil electrode. Others have achieved direct electron transfer between fructose dehydrogenase and metal electrodes, but these systems were highly unstable and no steady-state response was achieved. These results suggest that stable direct electron transfer is advantageously achieved with the membrane nestled in the membrane-like modified gold electrode surface of the present invention.

EXAMPLE 7

Measurement of Fructose Concentrations

To test the fructose dehydrogenase electrode in a real sensing application, the fructose concentration in apple and orange juice was measured. A calibration curve was prepared prior to each juice measurement. The juice samples were diluted in 10 mM $KH_2PO_4$ buffer, pH 4.5, to fall in the linear range of the calibration curve. Results from three different electrodes were averaged and compared to those obtained with an available enzymatic spectrophotometric assay kit. For apple juice, the electrodes yielded an average fructose concentration of 429 mM (n=12, where n equals number of juice measurements) compared to the assay kit value of 425 mM (n=2, where n equals number of assays). For orange juice, the electrodes measured an average fructose concentration of 127 mM (n=3) compared to the enzyme assay kit value of 124 mM (n=2). Relative standard deviations of 4.7 and 12.1% were obtained for the apple and orange juice samples, respectively. The close agreement between the electrode and assay kit measurements for fructose in orange juice are evidence of ascorbic acid blocking in a real sample environment.

EXAMPLE 8

Measurement of Sarcosine Concentrations

The sarcosine dehydrogenase electrode formed by immobilization in a lipid layer was immersed in a temperature-controlled electrochemical cell at 37 C with a Ag/AgCl reference electrode and a platinum auxiliary electrode. The solution was composed of 10 mM phosphate buffer, pH 7.5, and 0.08 mM phenazine methosulfate (PMS). The potential of the working electrode was held at 0.2 V versus the Ag/AgCl reference and aliquots of concentrated sarcosine solution (400 mM) were added to achieve the concentrations at which the steady state current measurements shown in FIG. 9 were taken. The current response was linear from <2 mM sarcosine to about 10 mM. The available range of sarcosine detection is from about 1 $\mu$M to 1 M.

EXAMPLE 9

Measurement of Creatine Concentrations

Creatinine amidohydrolase from Pseudomonas species, creatine amidinohydrolase from Pseudomonas species, and sarcosine dehydrogenase from Pseudomanas species, bovine serum albumin (BSA), creatinine, creatine, sarcosine, phenazine methosulfate, and 2,6-dichlorophenol indophenol were purchased from Sigma and used without further purification. 4,4'-diisothiocyanato-trans-stilbene-2,2'-disulfonic acid disodium salt (DIDS) was purchased from Fluka and glutaraldehyde was purchased from Fisher Scientific.

Electromechanical measurements were made with an Omni 90 potentiostat (Cypress Systems, Inc.). The Omni 90 was interfaced to a Macintosh IIcx with a National Instruments (Austin, Tex.) Lab-NB board software (Labview II). Gold disk electrodes or glassy carbon disk electrodes (d=1.6 mm, $A_{geom}$=0.02 cm$^2$) were used as the working electrode, while Ag/AgCl (3 M NaCl) electrode, and a platinum wire were used as the reference electrode and counter electrode, repectively. Amperometric measurements of creatinine, creatine, and sarcosine were done at 0.200 V vs. Ag/AgCl in stirred deoxygenated 100 mM $Kh_2PO_4/K_2HPO_4$, pH 7.5, under a blanket of argon at 37° C. Creatinine, creatine, or sarcosine was injected into the electrochemical cell using a 50 $\mu$l microsyringe.

Figure 17:
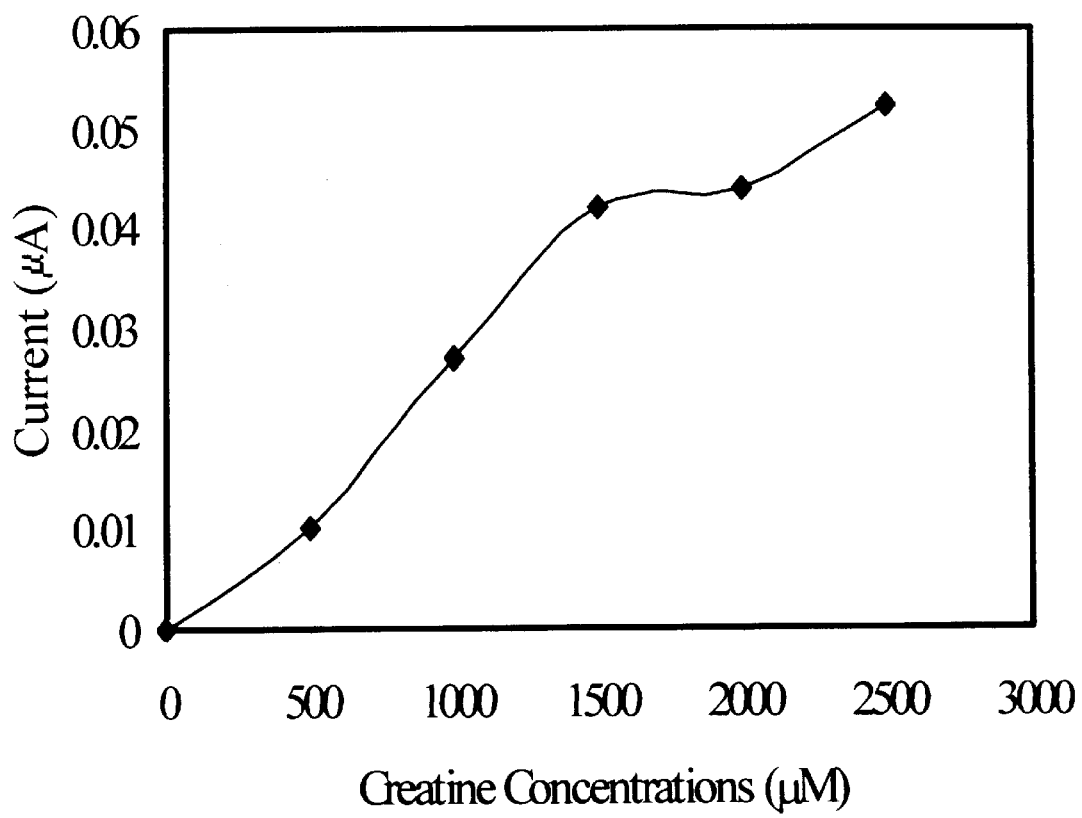
FIG. 17 depicts calibration curve for creatine determined by creatine sensor in 100 mM phosphate buffer (pH 7.5) with 0.500 mM 2,6-DCPIP at 37° C.

FIG. 17 shows a typical calibration curve for creatine using a creatine biosensor formed by glutaraldehyde crosslinking. When a stock solution containing creatine was injected with a 50 $\mu$l syringe into the electrochemical cell (37° C.) with the biosensor, Ag/AgCl reference electrode and platinum auxiliary electrode in 100 mM phosphate bffer (pH 7.5) with 0.5 mM 2,6-dichlorophenol indophenol (DCPIP), creatine permeated the enzyme layer and was decomposed first to sarcosine and finally to formaldehyde and glycine, while generating the reduced forms of the mediator, DCPIP. The reduced DCPIP then was oxidized by the electrode poised at 0.200 V vs Ag/AgCl. The curve shows strong, discernible current responses with each creatine injection until it reached its peak currents. The apparent $K_m$ of this creatine sensor was approximately 1000 $\mu$M according to the data in the figure, and it was well above the clinical range of 40–150 $\mu$M in normal humans. Thus, this physiological range is within the region for linear correlation of creatine concentrations with current readings.

EXAMPLE 10

Measurement of Creatinine Concentrations

Reagents and Materials. Creatinine amidohydrolase from Pseudomonas species, creatine amidinohydrolase from Pseudomonas species, and sarcosine dehydrogenase from Pseudomanas species, bovine serum albumin (BSA), reatinine, creatine, sarcosine, phenazine methosulfate, 2,6-dichlorophenol indophenol, were purchased from Sigma and used without further purification. 4,4'-diisothiocyanato-trans-stilbene-2,2'-disulfonic acid disodium salt (DIDS) was purchased from Fluka and glutaraldehyde was purchased from Fisher Scientific.

Electromechanical Measurements. Electromechanical measurements were made with an Omni 90 potentiostat (Cypress Systems, Inc.). The Omni 90 was interfaced to a Macintosh IIcx with a National Instruments (Austin, Tex.) Lab-NB board and software (Labview II). Gold disk electrodes or glassy carbon disk electrodes (d=1.6 mm, $A_{geom}$=0.02 cm$^2$) were used as the working electrode, while Ag/AgCl (3 M NaCl) electrode, and a platinum wire were used as the reference electrode and counter electrode, respectively. Amperometric measurements of creatinine, creatine, and sarcosine were done at 0.200 V vs. Ag/AgCl in stirred deoxygenated 100 mM $Kh_2PO_4/K_2HPO_4$, pH 7.5, under a blanket of argon at 37° C. Creatinine, creatine, or sarcosine was injected into the electrochemical cell using a 50 μl microsyringe.

Figure 18:
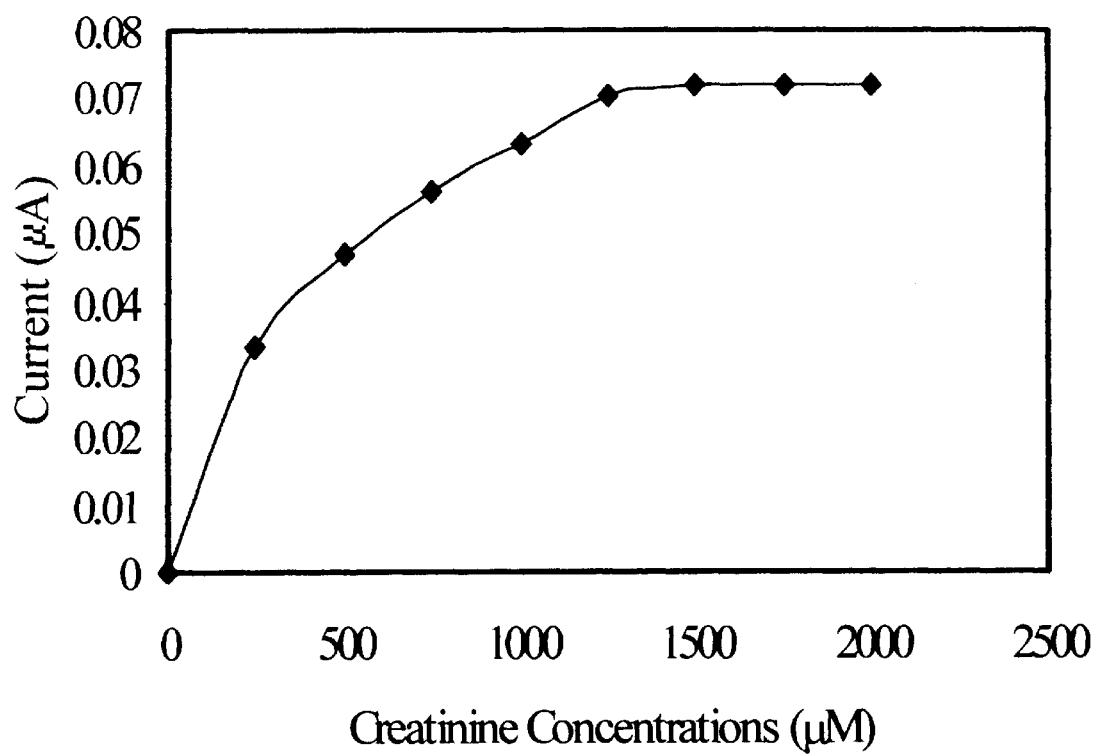
FIG. 18 depicts calibration curve for creatinine determined by creatinine sensor in 100 mM phosphate buffer (pH 7.5) with 5.00 mM 2,6-DCPIP at 37° C.

FIG. 18 shows characteristic amperometric responses for the creatinine sensor when creatinine was injected into the electrochemical cell under the same conditions as in Example 10, but with the creatinine biosensor formed by glutaraldehyde crosslinking. This curve displayed very rapid increase in anodic currents initially and then leveled out completely at approximately 1500 μM creatinine concentrations and the apparent $K_m$ for this sensor was roughly 250 μM, which is still well above the clinical range of 40–150 μM in humans. Although the activity of creatininase (100–300 units/mg) was much greater than that of both creatinase (10–15 units/mg) and sarcosine dehydrogenase (0.15–1.5 units/mg), which served as the limiting catalyst in this system, it is believed that the rate-determining step in this process was the transport of species through the gelatinous enzyme layer.

EXAMPLE 11

Construction of a MicroBiosensor

The present invention includes the construction amperometric microbiosensors that utilize oxygen-independent dehydrogenase enzymes. The biosensors of the present invention are modifications of those described in U.S. Pat. No. 5,611,900 issued to Worden et al., and which is incorporated by reference herein as to its relevant portions. These microsensors consists of a platinum wire drawn to a tip about 1–50 μM, which is sheathed in glass and plated with gold at the working end. The gold surface is modified as above to give a cell membrane-like layer with an embedded membrane-bound dehydrogase and co-immobilized electron acceptor. Metal electrodes with tips starting at 1 μM are available from World Precision Instruments. This working electrode then is inserted into a glass case drawn to a tip measuring from about 1 μm to 1 mm in diameter. The end may be protected by coating with Nafion or polyurethane polymer to further protect the working electrode from electroactive interfering agents and foulants. To complete the microsensor, a Ag/AgCl wire is inserted into the case to serve as both reference and counter electrode, and the case is filled with electrolyte. This microbiosensor construct eliminates the important drawback of oxygen dependence of the system based on a Clark-type oxygen microbiosensor.

Additionally, these microbiosensors are capable of the extremely fast response times desired for neurotransmitter measurements if the system can be used without a protective polymer film coating. The tradeoff is a less linear response to changes in analyte concentration than that that can be achieved by introducing some mass transfer influence on kinetics with a polymer film overlayer.

Further, although a particular form of the invention has been illustrated and described, it will be appreciated by those skilled in the art that various modifications can be made without departing from the spirit and scope of the invention. Accordingly, the scope of the present invention is not to be limited by the particular embodiments above, but is to be defined only by the appended claims and equivalents thereof.

I claim:

1. An amperometric biosensor for the measurement of the concentration of creatine, creatinine and/or sarcosine comprising:
    an electrode comprising a surface;
    an electronically active mediator deposited on the surface of the electrode; and
    a population of enzymes comprising either sarcosine dehydrogenase or sarcosine dehydrogenase and at least one hydrolase enzyme deposited on the surface of the electrode, wherein the population of enzymes is covalently linked.

2. The amperometric biosensor of claim 1, wherein the hydrolase enzyme is either creatine amidinohydrolase or a mixture of creatine amidinohydrolase and creatinine amidohydrolase.

3. The amperometric biosensor of claim 1, further comprising a stabilizer protein.

4. The amperometric biosensor of claim 3, wherein the stabilizer protein is bovine serum albumin (BSA).

5. The amperometric biosensor of claim 1, wherein the biosensor is miniaturized and further comprises:
    a metal wire with a working end plated with a noble metal or a carbon fiber;
    an electrode surface at the working end upon which sarcosine dehydrogenase and at least one hydrolase enzyme are immobilized to form a working electrode;
    an encasement containing the working electrode drawn to a tip of about 1–20 micrometers in diameter;
    a Ag/AgCl wire inserted into the encasement wherein the Ag/AgCl wire serves both as a reference and counter electrode;
    and an electrolyte filler inserted into the encasement.

6. The amperometric biosensor of claim 5, wherein the hydrolase enzyme is either creatine amidinohydrolase or creatinine amidohydrolase or a mixture of both creatine amidinohydrolase or creatinine amidohydrolase.

7. The amperometric biosensor of claim 1, wherein the electrode is either metallic or non-metallic.

8. The amperometric biosensor of claim 7, wherein the metallic electrode is gold, silver, platinum or palladium.

9. The amperometric biosensor of claim 7, wherein the non-metallic electrode comprises carbon.

10. The amperometric biosensor of claim 1, further comprising a chemisorbed lipophilic layer deposited on the surface of the electrode.

11. The amperometric biosensor of claim 10, wherein the lipophilic layer comprises a thiol.

12. The amperometric biosensor of claim 1, further comprising an amphiphilic lipid deposited on the surface of the electrode.

13. The amperometric biosensor of claim 12, wherein the amphiphilic lipid is a phospholipid.

14. The method of using an amperometric biosensor to measure the concentration of creatine, creatinine and/or sarcosine comprising:

assembling the amperometric biosensor of claim 1;

providing a sample; and measuring the current produced by oxidation of any sarcosine, creatine and/or creatinine present in the sample.

15. The method of claim 14, further comprising adding a stabilizer protein to the amperometric biosensor prior to measuring the current.

16. The method of claim 14, wherein the electrode is metallic or non-metallic.

17. A method of preparing an amperometric biosensor capable of measuring the concentration of creatine, creatinine and/or sarcosine comprising:

adding a covalent linking agent to a mixture of sarcosine dehydrogenase and at least one hydrolase enzyme to form a population of substantially covalently linked enzymes;

depositing the population of covalently linked enzymes on an electrode surface; and adding an electronically active mediator to the population of enzymes either before or after the enzymes are deposited on the electrode surface.

18. The method of claim 17, further comprising adding a protein stabilizer to the mixture of enzymes.

19. The method of claim 18, wherein the protein stabilizer is bovine serum albumin (BSA).

20. An amperometric biosensor for the measurement of the concentration of creatine, creatinine and/or sarcosine comprising:

an metallic electrode comprising a surface;

a chemisorbed lipophilic layer deposited onto the electrode surface;

an electronically active mediator added to the lipophilic layer; and a population of redox enzymes comprising sarcosine dehydrogenase and a hydrolase enzyme deposited onto the lipophilic layer.

21. The amperometric biosensor of claim 20, wherein the hydrolase enzyme is either creatine amidinohydrolase or creatinine amidohydrolase or a mixture of both creatine amidinohydrolase or creatinine amidohyrolase.

22. The amperometric biosensor of claim 20, wherein the lipophilic layer comprises a thiol.

23. The amperometric biosensor of claim 20, further comprising an amphiphilic lipid deposited on the surface of the electrode.

24. The amperometric biosensor of claim 20, wherein the amphiphilic lipid is a phospholipid.

25. The method of using an amperometric biosensor to measure the concentration of creatine, creatinine and/or sarcosine comprising:

assembling the amperometric biosensor of claim 20;

providing a sample; and measuring the current produced by oxidation of any sarcosine, creatine and/or creatinine present in the sample.

26. The biosensor of claim 20, wherein the hydrolase enzyme is either creatine amidinohydrolase or a mixture of creatine amidohydrolase and creatinine amidohydrolase.

27. A method of preparing an amperometric biosensor capable of measuring the concentration of creatine, creatinine and/or sarcosine comprising:

preparing a metallic electrode surface by adding a lipophilic layer via chemisorption;

depositing a mixture of sarcosine dehydrogenase and at least one hydrolase enzyme to form a population of immobilized enzymes on the electrode surface; and adding an electronically active mediator to the population of enzymes either before or after the enzymes are deposited on the electrode surface.

* * * * *